United States Patent
Agarwal et al.

(10) Patent No.: US 11,481,033 B1
(45) Date of Patent: Oct. 25, 2022

(54) WEARABLE DEVICES WITH INTERFERING BLADDERS FOR CREATING HAPTIC FEEDBACK

(71) Applicant: META PLATFORMS TECHNOLOGIES, LLC, Menlo Park, CA (US)

(72) Inventors: Priyanshu Alan Agarwal, Kirkland, WA (US); Nicholas Roy Corson, Woodinville, WA (US); Nicholas Colonnese, Kirkland, WA (US); Zachary Daniel West, Seattle, WA (US); Aaron Alan Ambuske, Seattle, WA (US); John Dietrich Martin, Seattle, WA (US); Ana Mirona Motoc, Seattle, WA (US); Brian Fletcher, Issaquah, WA (US); Jay Barrett Willet, Tacoma, WA (US)

(73) Assignee: META PLATFORMS TECHNOLOGIES, LLC, Menlo Park, CA (US)

( * ) Notice: Subject to any disclaimer, the term of this patent is extended or adjusted under 35 U.S.C. 154(b) by 0 days.

(21) Appl. No.: 17/026,103

(22) Filed: Sep. 18, 2020

Related U.S. Application Data

(60) Provisional application No. 62/911,800, filed on Oct. 7, 2019.

(51) Int. Cl.
*G06F 3/01* (2006.01)
*A61M 21/00* (2006.01)
*A61H 9/00* (2006.01)

(52) U.S. Cl.
CPC .............. *G06F 3/016* (2013.01); *A61M 21/00* (2013.01); *G06F 3/014* (2013.01); *A61H 9/0078* (2013.01); *A61M 2021/0022* (2013.01); *A61M 2205/0216* (2013.01); *A61M 2209/088* (2013.01)

(58) Field of Classification Search
CPC ........ G06F 3/016; G06F 3/014; A61M 21/00; A61M 2021/0022; A61M 2205/0216; A61M 2209/088; A61H 9/0078
See application file for complete search history.

(56) References Cited

U.S. PATENT DOCUMENTS

| 2016/0363997 | A1 | 12/2016 | Black et al. | |
| 2018/0107277 | A1* | 4/2018 | Keller | G06F 3/016 |
| 2021/0096649 | A1* | 4/2021 | Mok | G06F 3/016 |

* cited by examiner

*Primary Examiner* — Towfiq Elahi
(74) *Attorney, Agent, or Firm* — Morgan, Lewis & Bockius LLP

(57) ABSTRACT

A wearable device for providing haptic stimulations is provided. The wearable device includes: (i) a wearable structure to be worn on a portion of a user's body and (ii) an inflatable bladder, coupled to the wearable structure, that includes two or more pockets positioned at a target location on the wearable structure. Furthermore, the two or more pockets are configured to, when inflated, impart directional force(s) onto the user at the target location that impede movement of the portion of the user's body. Additionally, the directional force(s) are caused by the two or more pockets interfering with each other, when inflated. In some embodiments, (a) the portion of the user's body is a hand of the user, (b) the target location is a finger joint on the user's hand, and (c) the directional force(s) imparted onto the user at the target location impede flexion of the user's finger.

19 Claims, 20 Drawing Sheets

T2<T1
h2>h1

WEARABLE DEVICES WITH INTERFERING BLADDERS FOR CREATING HAPTIC FEEDBACK

RELATED APPLICATION

This application claims priority to U.S. Provisional Application Ser. No. 62/911,800, filed Oct. 7, 2019, entitled "Wearable Devices with Interfering Bladders for Creating Haptic Feedback," which is incorporated by reference herein in its entirety.

TECHNICAL FIELD

This application relates generally to haptic stimulations, including creating haptic stimulations on users of artificial-reality devices.

BACKGROUND

Artificial-reality devices (e.g., virtual-reality devices, augmented-reality devices, etc.) have wide applications in various fields, including engineering design, medical surgery practice, military simulated practice, and video gaming. Haptic or kinesthetic stimulations recreate the sense of touch by applying forces, vibrations, and/or motions to a user, and are frequently implemented with artificial-reality devices in the form of a wearable device (sometimes referred to as a "haptic display" or a "haptic device").

At a high level, haptic displays can by placed into two broad categories: (i) rigid haptic displays and (ii) soft haptic displays. Rigid haptic displays are typically exoskeleton-type displays that are bulky and not feasible for commercial artificial-reality systems, especially when placed on user's hand due to their high encumbrance. Soft haptic displays offer more promise because these haptic displays include soft elements, meaning these devices have low encumbrance and are thus better suited for artificial-reality systems. Within the soft haptic display category, a majority of the displays use tendons to render haptic feedback. Doing so, however, induces unnatural parasitic forces at a target location, which significantly lowers the sensory and perceptual believability of the haptic feedback. Existing non-tendon type soft displays either have high encumbrance, low dynamic range due to issues like buckling of the soft actuator, or are perceptually not appealing. Therefore, existing non-tendon type soft displays are not practically useful in artificial-reality systems.

SUMMARY

Accordingly, there is a need for devices and systems that can create haptic stimulations on a user without (i) encumbering the user and (ii) detracting from the artificial-reality experience. One solution is a wearable device that includes novel soft haptic actuators that do not suffer from the drawbacks of existing designs. The designs discussed herein have low encumbrance, moderate dynamic range, and can render interactions that are perceptually believable. The soft haptic actuators discussed herein include one or more inflatable bladders that are configured to expand and contract according to fluid pressure within each bladder. Each bladder is made from flexible, durable materials that do not encumber the user but are still able to create adequate haptic stimulations. Further, the bladders are airtight so that a pressure inside the bladders can be varied to create various haptic stimulations (e.g., a bladder can transition rapidly between unpressurized and pressurized states, or vice versa). By changing the pressure, a respective bladder can go from being unpressurized and unnoticed, to being pressurized, and it is this transition that creates the haptic stimulations felt by the user. Importantly, the haptic stimulations felt by the user can correspond to media presented to the user by an artificial-reality system (e.g., virtual-reality or augmented-reality devices).

(A1) In some embodiments, the solution explained above can be implemented on a wearable device that includes: (i) a wearable structure to be worn on a portion of a user's body, and (ii) at least one inflatable bladder, coupled to the wearable structure, that includes two or more pockets positioned at a target location on the wearable structure. In such embodiments, the two or more pockets are configured to, when inflated, impart one or more directional forces onto the user at the target location that impede movement of the portion of the user's body. Furthermore, the one or more directional forces are caused by the two or more pockets interfering with each other, when inflated.

(A2) In accordance with some embodiments, a method is provided. The method is performed by the wearable device of (A1). The method includes receiving an instruction from a computer system (e.g., from the computer system 130 in FIG. 1) to change fluid pressure in the least one inflatable bladder. The instruction from the computer system corresponds to media presented to the user by the computer system. The method further includes, in response to receiving the instruction, activating a pressure source to change the fluid pressure in the least one inflatable bladder according to the instruction. In some embodiments, the least one inflatable bladder delivers (e.g., imparts) a haptic stimulation to the user wearing the wearable structure when the two or more pockets of the bladder expand a threshold amount. To further illustrate, the wearable device of (A1) can be in communication with a computer system (e.g., an augmented-reality device and/or a virtual-reality device, such as the devices described in FIGS. 10 and 11), and the wearable device can stimulate the body based on an instruction from the computer system. As an example, the computer system may display media content to a user (e.g., via a head-mounted display), and the computer system may also instruct the wearable device to create haptic stimulations that correspond to the media content displayed to the user and/or other information collected by the wearable device (e.g., via sensors included with the wearable device) and/or the head-mounted display. In some embodiments, the computer system activates the pressure source instead of the wearable device.

(A3) In some embodiments of any of A1 or A2, the two or more pockets include (i) a first pocket with an end portion and a body portion and (ii) a second pocket with an end portion and a body portion. In such embodiments, (i) the end portion of the second pocket is coupled with the end portion of the first pocket to form a connection point, and (ii) the body portion of the second pocket is decoupled from the body portion of the first pocket.

(A4) In some embodiments of A3, when the two or more pockets are inflated, the first and second pockets are configured to expand such that the body portion of the second pocket and the body portion of the first pocket fan out away from the connection point. Furthermore, when the two or more pockets are not inflated, the first and second pockets are configured to collapse such that the body portion of the second pocket and the body portion of the first pocket are adjacent to each other (i.e., the first and second pockets lay flat, or are at least capable of laying flat).

(A5) In some embodiments of any of A1 or A2, the at least one inflatable bladder further comprises an elongated substrate forming a first side of the respective inflatable bladder. In such embodiments, the two or more pockets (i) are coupled to and distributed along a length of the elongated substrate and (ii) form a second side of the respective inflatable bladder. In some embodiments, one or more sidewalls extend because the first side and the second side of the respective inflatable bladder. In such cases, the elongated substrate may form the one or more sidewalls.

(A6) In some embodiments of A5, when the two or more pockets are inflated, each (or some subset of pockets) pocket is configured to expand and interfere with at least one other pocket (e.g., a neighboring pocket distributed along the length of the elongated substrate) of the two or more pockets. For example, pockets from the two or more pockets positioned at a finger joint interfere with each other when the user bends his or her finger. Furthermore, when the two or more pockets are not inflated, the two or more pockets do not impede free movement of the portion of the user's body.

(A7) In some embodiments of any of A5 or A6, the elongated substrate has a first elasticity, and the two or more pockets have a second elasticity that is greater than the first elasticity.

(A8) In some embodiments of A7, the elongated substrate is made from an inelastic textile, and the two or more pockets are made from an elastic polymer.

(A9) In some embodiments of any of A5-A8, the portion of the user's body is a hand of the user, and the elongated substrate is sized to fit along a palmar side of a first finger of the user's hand.

(A10) In some embodiments of any of A1-A9, the portion of the user's body is a hand of the user. In such embodiments, the target location is a finger joint on the user's hand and the one or more directional forces imparted onto the user at the target location impede flexion of the user's finger. The one or more directional forces imparted onto the user at the target location simulate (i.e., mimic) forces induced by physical objects at the finger joint during natural hand-object interaction.

(A11) In some embodiments of any of A1-A10, the wearable device further includes a grounding assembly that is configured to secure the wearable structure and the at least one inflatable bladder to the user's body.

(A12) In some embodiments of any of A1-A11, the two or more pockets have a predefined shape when inflated to a predefined pressure, and the predefined shape is dependent, at least in part, on a wall thickness of each pocket of the two or more pockets.

(A13) In some embodiments of any of A1-A12, the at least one inflatable bladder is fluidically coupled to a source, and the two or more pockets are further configured to (i) receive a fluid from the source and (ii) expand in proportion with a fluid pressure inside each pocket.

(A14) In some embodiments of A13, the wearable device also includes a switchable valve that is configured to switch between an open state and a closed state. In such embodiments, the switchable valve prevents the fluid from exiting (or entering) the two or more pockets when in the closed state. For example, a pressure inside the at least one inflatable bladder may be increased to some threshold pressure, and in doing so, the two or more pockets expand by some amount. At this point, the switchable valve is switch from the open state to the closed state, so that fluid inside the inflatable bladder cannot escape, e.g., in response to a user's attempt to move the portion of his or her body.

(A15) In some embodiments of any of A1-A14, the source is in communication with a computing device, and the source is configured to change the fluid pressure of the two or more pockets in response to receiving one or more signals from the computing device. In some embodiments, the computing device also controls the switchable valve.

(A16) In some embodiments of A15, the computing device is in communication with a head-mounted display that presents content to the wearer, the head-mounted display including an electronic display, and the one or more signals correspond to content displayed on the electronic display.

(A17) In some embodiments of any of A15 or A16, the wearable device also includes one or more sensors, coupled to the wearable structure, configured to generate spatial and motion data corresponding to the user's movements. In such embodiments, the spatial and motion data are communicated to the computing device.

(A18) In some embodiments of A17, the one or more signals further correspond to the spatial and motion data corresponding to the user's movements, and the one or more signals are generated by the computing device to impede movement of the portion of the user's body.

(A19) In some embodiments of any of A1-A18, a magnitude of the one or more directional forces corresponds to a fluid pressure inside the two or more pockets and a change in geometry of the two or more pockets caused by the two or more pockets interfering with each other.

(A20) In some embodiments of any of A1-A19, the one or more directional forces imparted onto the user at the target location simulate forces induced by physical objects at the target location (e.g., a finger joint) during natural-object interaction.

(A21) In another aspect, an artificial-reality device is provided that includes a computer, a fluid/pressure source in communication with the computer, and a haptic device in communication with the computer. The haptic device has the structure of the wearable device of A1-A19. The artificial-reality device is configured to perform any of A1-A20. An alternative artificial-reality device includes a wearable device, a source in communication with the wearable device, and a compute in communication with the wearable device. In these embodiments, the wearable device has the structure of the wearable device of A1-A20. Furthermore, the artificial-reality device system is configured to perform any of A1-A20.

(A22) In yet another aspect, one or more wearable devices are provided and the one or more wearable devices include means for performing any one of A1-A20.

(A23) In still another aspect, a non-transitory computer-readable storage medium is provided (e.g., as a memory device, such as external or internal storage, that is in communication with a wearable device). The non-transitory computer-readable storage medium stores executable instructions that, when executed by a computer with one or more processors/cores, cause the computer to perform any one of A1-A20.

(B1) In accordance with some embodiments, another wearable device is provided that includes: (i) a wearable structure to be worn on a portion of a user's body, and (ii) an inflatable bladder, coupled to the wearable structure at a target location, that includes opposing first and second surfaces, the inflatable bladder being configured to receive a fluid from a source. In such embodiments, the first surface of the inflatable bladder includes a plurality of barbs positioned to interact with the user's body at the target location, whereby the plurality of barbs are configured to protrude from the first surface in response to the inflatable bladder receiving the fluid from the source.

(B2) In accordance with some embodiments, a method is provided. The method is performed by the wearable device of (B1). The method includes receiving an instruction from a computer system (e.g., from the computer system 130 in FIG. 1) to change fluid pressure in the inflatable bladder. The instruction from the computer system corresponds to media presented to the user by the computer system. The method further includes, in response to receiving the instruction, activating a pressure source to change the fluid pressure in the inflatable bladder according to the instruction. In some embodiments, the inflatable bladder delivers (e.g., imparts) a haptic stimulation to the user wearing the wearable structure when the bladder expand a threshold amount. To further illustrate, the wearable device of (B1) can be in communication with a computer system (e.g., an augmented-reality device and/or a virtual-reality device, such as the devices described in FIGS. 10 and 11), and the wearable device can stimulate the body based on an instruction from the computer system. As an example, the computer system may display media content to a user (e.g., via a head-mounted display), and the computer system may also instruct the wearable device to create haptic stimulations that correspond to the media content displayed to the user and/or other information collected by the wearable device (e.g., via sensors included with the wearable device) and/or the head-mounted display. In some embodiments, the computer system activates the pressure source instead of the wearable device.

(B3) In some embodiments of any of B1 or B2, the first surface of the inflatable bladder transitions from a concave shape to a convex shape in response to the inflatable bladder receiving the fluid from the source.

(B4) In some embodiments of B3, the convex shape of the first surface causes the plurality of barbs to protrude from the first surface.

(B5) In some embodiments of any of B3 or B4, the concave shape of the first surface of the inflatable bladder complements a profile of the user's body at the target location.

(B6) In some embodiments of any of B1-B5, barbs in the plurality of barbs are arranged in the predefined pattern, and the predefined pattern is defined according to a profile of the user's body at the target location.

(B7) In some embodiments of B6, respective shapes of the barbs in the plurality of barbs are also defined according to the profile of the user's body at the target location.

(B8) In some embodiments of any of B6 or B7, respective depths of the barbs in the plurality of barbs are defined according to the profile of the user's body at the target location.

(B9) In some embodiments of any of B1-B8, the first surface of the inflatable bladder is made from an elastic material, and the second surface of the inflatable bladder is (i) made from an inelastic material and (ii) positioned to not interact with the portion of the user's body (i.e., the second surface of the inflatable bladder faces away from the user's body).

(B10) In some embodiments of any of B1-B9, a roughness (bumpiness, coarseness) of the first surface of the inflatable bladder increases with a fluid pressure inside the inflatable bladder.

(B11) In some embodiments of B10, the first surface of the inflatable bladder is configured to have a maximum roughness when the fluid pressure inside the inflatable bladder reaches a maximum pressure.

(B12) In some embodiments of any of B1-B11, the plurality of barbs included with the first surface of the inflatable bladder is further configured to impart a haptic stimulation to the user's body at the target location in response to the inflatable bladder receiving the fluid from the source (e.g., when the fluid pressure inside the inflatable bladder satisfies a threshold pressure).

(B13) In some embodiments of any of B1-B12, the first surface of the inflatable bladder has a first texture when the fluid pressure inside the inflatable bladder is at a first pressure. For example, the first surface of the inflatable bladder has a uniform, soft texture. In contrast, the first surface of the inflatable bladder has a second texture when the fluid pressure inside the inflatable bladder is at a second pressure greater than the first pressure. For example, the first surface of the inflatable bladder has a spiked, firm texture, caused by the plurality of barbs protruding from the first surface.

(B14) In some embodiments of any of B1-B13, when the inflatable bladder is in a first pressurized state, the first surface of the inflatable bladder is adjacent to the second surface of the inflatable bladder. Furthermore, in the first pressurized state, the plurality of barbs are in a default-planar state such that, to a human touch, the plurality of barbs feel smooth and uniform. When the inflatable bladder is in a second pressurized state, the first surface of the inflatable bladder bulges away from the second surface of the inflatable bladder, causing the plurality of barbs to protrude from the first surface. Put another way, when the inflatable bladder is pressurized, the inflatable bladder behaves similar to a pufferfish, in that the first surface of the inflatable bladder inflates and becomes spiked. Note that the second surface is static/elastic and, consequently, the second surface does not bulge. Because the second surface remains more or less planar, even when the inflatable bladder is pressurized, the first surface is able to expand (i.e., displace) a significant amount.

(B15) In some embodiments of B14, when the inflatable bladder is in the first pressurized state, first distances separate barbs in the plurality of barbs (more specifically, the first distances separate tips of the plurality of barbs). When the inflatable bladder is in the second pressurized state, second distances greater than the first distances separate the barbs in the plurality of barbs (more specifically, the second distances separate tips of the plurality of barbs).

(B16) In some embodiments of any of B1-B15, the source is in communication with a computing device, and the source is configured to change the fluid pressure of the two or more pockets in response to receiving one or more signals from the computing device. In some embodiments, the computing device also controls the switchable valve.

(B17) In some embodiments of B16, the computing device is in communication with a head-mounted display that presents content to the wearer, the head-mounted display including an electronic display, and the one or more signals correspond to content displayed on the electronic display.

(B18) In some embodiments of any of B16 or B11, the wearable device also includes one or more sensors, coupled to the wearable structure, configured to generate spatial and motion data corresponding to the user's movements. In such embodiments, the spatial and motion data are communicated to the computing device.

(B19) In some embodiments of B18, the one or more signals further correspond to the spatial and motion data corresponding to the user's movements, and the one or more signals are generated by the computing device to impede movement of the portion of the user's body.

(B20) In some embodiments of any of B1-B19, the wearable device further includes a second inflatable bladder, coupled to the wearable structure at a different target location, configured to receive the fluid from the source. In such embodiments, a surface of the second inflatable bladder includes a second plurality of barbs positioned to interact with the user's body at the different target location, the second plurality of barbs being configured to protrude from the surface in response to the second inflatable bladder receiving the fluid from the source. In some embodiments, the first plurality of barbs are arranged in a pattern that differs from a pattern of the second plurality of barbs. For example, the first plurality of barbs are arrangement in a pattern that is optimize for the target location while the second plurality of barbs are arrangement in a pattern that is optimize for the different target location.

(B21) In another aspect, an artificial-reality device is provided that includes a computer, a fluid/pressure source in communication with the computer, and a haptic device in communication with the computer. The haptic device has the structure of the wearable device of A1-A19. The artificial-reality device is configured to perform any of B1-B19. An alternative artificial-reality device includes a wearable device, a source in communication with the wearable device, and a compute in communication with the wearable device. In these embodiments, the wearable device has the structure of the wearable device of B1-B19. Furthermore, the artificial-reality device system is configured to perform any of B1-B19.

(B22) In yet another aspect, one or more wearable devices are provided and the one or more wearable devices include means for performing any one of B1-B19.

(B23) In still another aspect, a non-transitory computer-readable storage medium is provided (e.g., as a memory device, such as external or internal storage, that is in communication with a wearable device). The non-transitory computer-readable storage medium stores executable instructions that, when executed by a computer with one or more processors/cores, cause the computer to perform any one of B1-B19.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures and specification.

DESCRIPTION OF EMBODIMENTS

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are used only to distinguish one element from another. For example, a first bladder could be termed a second bladder, and, similarly, a second bladder could be termed a first bladder, without departing from the scope of the various described embodiments. The first bladder and the second bladder are both bladders, but they are not the same bladder.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, the term "if" means "when" or "upon" or "in response to determining" or "in response to detecting" or "in accordance with a determination that," depending on the context. Similarly, the phrase "if it is determined" or "if [a stated condition or event] is detected" means "upon determining" or "in response to determining" or "upon detecting [the stated condition or event]" or "in response to detecting [the stated condition or event]" or "in accordance with a determination that [a stated condition or event] is detected," depending on the context.

As used herein, the term "exemplary" is used in the sense of "serving as an example, instance, or illustration" and not in the sense of "representing the best of its kind."

Figure 1:
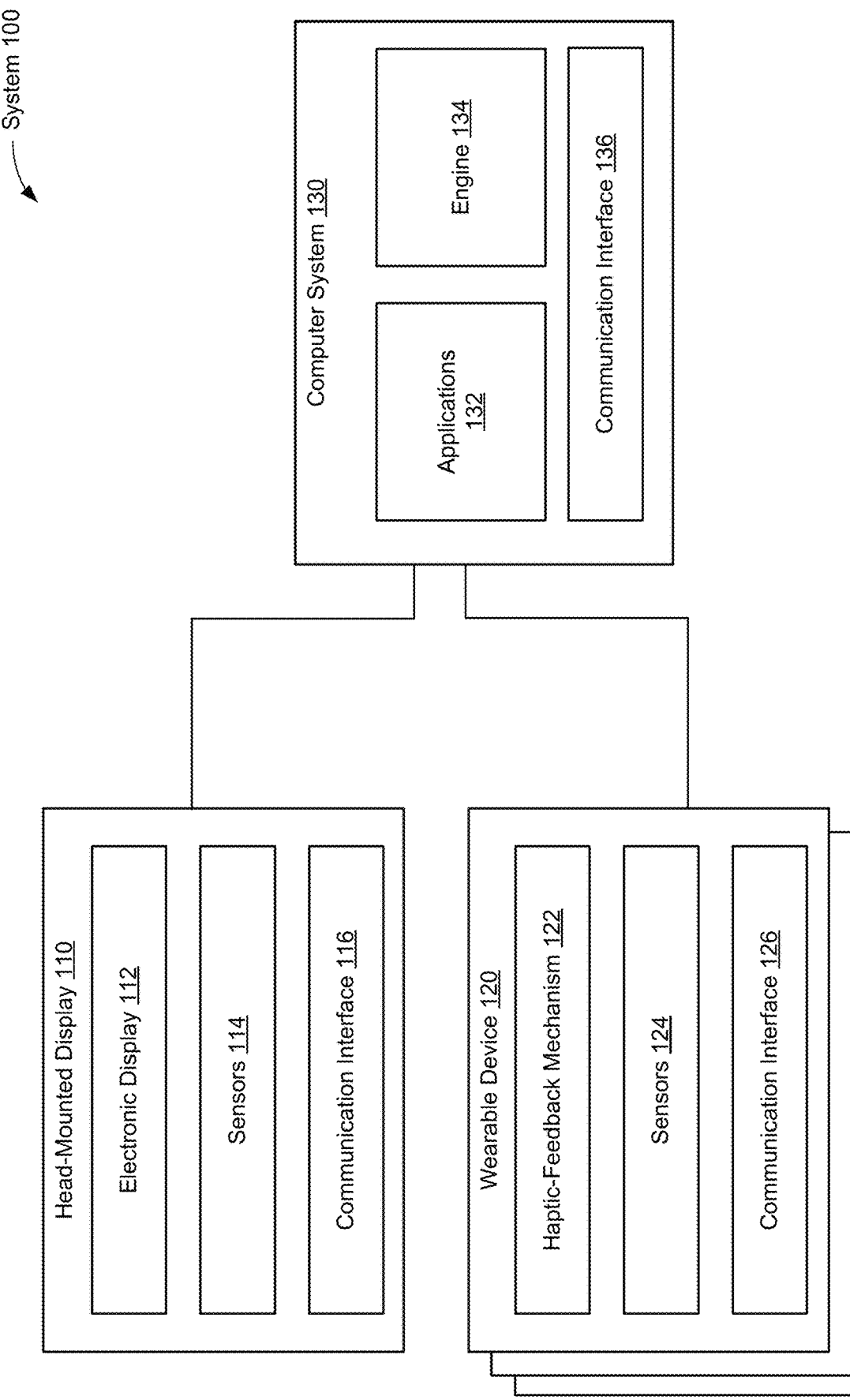
FIG. 1 is a block diagram illustrating an example haptics system, in accordance with various embodiments.

FIG. 1 is a block diagram illustrating an artificial-reality system 100 in accordance with various embodiments. While some example features are illustrated, various other features have not been illustrated for the sake of brevity and so as not to obscure pertinent aspects of the example embodiments disclosed herein. To that end, as a non-limiting example, the system 100 includes one or more wearable devices 120 (sometimes referred to as "wearable apparatuses," or simply "apparatuses"), which are used in conjunction with a computer system 130 (sometimes referred to as a "computer device" or a "remote computer device") and a head-mounted display 110. In some embodiments, the system 100 provides the functionality of a virtual-reality device with haptic feedback, an augmented-reality device with haptic feedback, a mixed-reality device with haptic feedback, or a combination thereof. The head-mounted display 110 presents media to a user. Examples of media presented by the head-mounted display 110 include images, video, audio, or some combination thereof. In some embodiments, audio is presented via an external device (e.g., speakers and/or headphones), which receives audio information from the head-mounted display 110, the computer system 130, or both, and presents audio data based on the audio information.

The head-mounted display 110 includes an electronic display 112, sensors 114, and a communication interface 116. The electronic display 112 displays images to the user in accordance with data received from the computer system 130. In various embodiments, the electronic display 112 comprises a single electronic display 112 or multiple electronic displays 112 (e.g., one display for each eye of a user).

The sensors 114 include one or more hardware devices that detect spatial and motion information about the head-mounted display 110. Spatial and motion information can include information about the position, orientation, velocity, rotation, and acceleration of the head-mounted display 110. For example, the sensors 114 may include one or more inertial measurement units (IMUs) that detect rotation of the user's head while the user is wearing the head-mounted display 110. This rotation information can then be used (e.g., by the engine 134) to adjust the images displayed on the electronic display 112. In some embodiments, each IMU includes one or more gyroscopes, accelerometers, and/or magnetometers to collect the spatial and motion information. In some embodiments, the sensors 114 include one or more cameras positioned on the head-mounted display 110.

The communication interface 116 enables input and output to the computer system 130. In some embodiments, the communication interface 116 is a single communication channel, such as HDMI, USB, VGA, DVI, or DisplayPort. In other embodiments, the communication interface 116 includes several distinct communication channels operating together or independently. In some embodiments, the communication interface 116 includes hardware capable of data communications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, or MiWi) and/or any other suitable communication protocol. The wireless and/or wired connections may be used for sending data collected by the sensors 114 from the head-mounted display to the computer system 130. In such embodiments, the communication interface 116 may also receive audio/visual data to be rendered on the electronic display 112.

The wearable device 120 includes a wearable structure worn by the user (e.g., a glove, a shirt, wristband, pants, etc.). In some embodiments, the wearable device 120 collects information about a portion of the user's body (e.g., the user's hand) that can be used as input for artificial-reality applications 132 executing on the computer system 130. In the illustrated embodiment, the wearable device 120 includes a haptic-feedback mechanism 122, sensors 124, and a communication interface 126. The wearable device 120 may include additional components that are not shown in FIG. 1, such as a power source (e.g., an integrated battery, a connection to an external power source, a container containing compressed air, or some combination thereof), one or more processors, memory, a display, microphones, and speakers.

The haptic-feedback mechanism 122 provides haptic feedback (i.e., haptic stimulations) to a portion of the user's body (e.g., hand, wrist, arm, leg, etc.). The haptic feedback may be a vibration stimulation, a pressure stimulation, or some combination thereof. To accomplish this, the haptic-feedback mechanism 122 includes one or more inflatable bladders 204, each of which is configured to inflate and apply a force to the portion of the user's body. Various embodiments of the haptic-feedback mechanism 122 are described with reference to FIGS. 3A through 8C. It is also noted that the haptic-feedback mechanism 122 may be used to improve coupling (e.g., fit) of the wearable device 120 to the user. For example, instead of (or in addition to) providing a haptic stimulation, one or more bladders 204 of the plurality of inflatable bladders 204 are inflated to varying degrees such that contact is made with the user's body. The contacting bladders prevent the wearable device 120 from moving (e.g., sliding or rotating) when attached to the user's body.

In some embodiments, the sensors 124 include one or more hardware devices that detect spatial and motion information about the wearable device 120. Spatial and motion information can include information about the position, orientation, velocity, rotation, and acceleration of the wearable device 120 or any subdivisions of the wearable device 120, such as fingers, fingertips, knuckles, the palm, or the wrist when the wearable device 120 is worn near the user's hand. The sensors 124 may be IMUs, as discussed above with reference to the sensors 114. The sensors 124 may include one or more hardware devices that monitor a state of a respective bladder 204 of the haptic-feedback mechanism 122.

The communication interface 126 enables input and output to the computer system 130. In some embodiments, the communication interface 126 is a single communication channel, such as USB. In other embodiments, the communication interface 126 includes several distinct communication channels operating together or independently. For example, the communication interface 126 may include separate communication channels for receiving control signals for the haptic-feedback mechanism 122 and sending data from the sensors 124 to the computer system 130. The one or more communication channels of the communication interface 126 can be implemented as wired or wireless connections. In some embodiments, the communication interface 126 includes hardware capable of data communications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, or MiWi), custom or standard wired protocols (e.g., Ethernet or HomePlug), and/or any other suitable communication protocol, including communication protocols not yet developed as of the filing date of this document.

The computer system 130 is a computing device that executes artificial-reality applications (e.g., virtual-reality applications, augmented-reality applications, or the like) to process input data from the sensors 114 on the head-mounted display 110 and the sensors 124 on the wearable device 120. The computer system 130 provides output data for (i) the electronic display 112 on the head-mounted display 110 and (ii) the haptic-feedback mechanism 122 on the wearable device 120.

The computer system includes a communication interface 136 that enables input and output to other devices in the system 100. The communication interface 136 is similar to the communication interface 116 and the communication interface 126.

In some embodiments, the computer system 130 sends instructions (e.g., the output data) to the wearable device 120. In response to receiving the instructions, the wearable device 120 creates one or more haptic stimulations (e.g., activates one or more of the bladders 204). Alternatively, in some embodiments, the computer system 130 sends instructions to an external device, such as a fluid (pressure) source (e.g., source 210, FIG. 2), and in response to receiving the instructions, the external device creates one or more haptic stimulations (e.g., the output data bypasses the wearable device 120). Alternatively, in some embodiments, the computer system 130 sends instructions to the wearable device 120, which in turn sends the instructions to the external device. The external device then creates one or more haptic stimulations by adjusting fluid pressure in one or more of the bladders 204. Although not shown, in the embodiments that include a distinct external device, the external device may be connected to the head-mounted display 110, the wearable device 120, and/or the computer system 130 via a wired or wireless connection. The external device may be a pneumatic device, a hydraulic device, some combination thereof, or any other device capable of adjusting pressure.

The computer system 130 can be implemented as any kind of computing device, such as an integrated system-on-a-chip, a microcontroller, a desktop or laptop computer, a server computer, a tablet, a smart phone or other mobile device. Thus, the computer system 130 includes components common to typical computing devices, such as a processor, random access memory, a storage device, a network interface, an I/O interface, and the like. The processor may be or include one or more microprocessors or application specific integrated circuits (ASICs). The memory may be or include RAM, ROM, DRAM, SRAM and MRAM, and may include firmware, such as static data or fixed instructions, BIOS, system functions, configuration data, and other routines used during the operation of the computing device and the processor. The memory also provides a storage area for data and instructions associated with applications and data handled by the processor.

The storage device provides non-volatile, bulk, or long term storage of data or instructions in the computing device. The storage device may take the form of a magnetic or solid state disk, tape, CD, DVD, or other reasonably high capacity addressable or serial storage medium. Multiple storage devices may be provided or available to the computing device. Some of these storage devices may be external to the computing device, such as network storage or cloud-based storage. The network interface includes an interface to a network and can be implemented as either wired or wireless interface. The I/O interface interfaces the processor to peripherals (not shown) such as, for example and depending upon the computing device, sensors, displays, cameras, color sensors, microphones, keyboards, and USB devices.

In the example shown in FIG. 1, the computer system 130 further includes artificial-reality applications 132 and an artificial-reality engine 134. In some embodiments, the artificial-reality applications 132 and the artificial-reality engine 134 are implemented as software modules that are stored on the storage device and executed by the processor. Some embodiments of the computer system 130 include additional or different components than those described in conjunction with FIG. 1. Similarly, the functions further described below may be distributed among components of the computer system 130 in a different manner than is described here.

Each artificial-reality application 132 is a group of instructions that, when executed by a processor, generates virtual-reality content for presentation to the user. A artificial-reality application 132 may generate artificial-reality content in response to inputs received from the user via movement of the head-mounted display 110 or the wearable device 120. Examples of artificial-reality applications 132 include gaming applications, conferencing applications, and video playback applications.

The artificial-reality engine 134 is a software module that allows artificial-reality applications 132 to operate in conjunction with the head-mounted display 110 and the wearable device 120. In some embodiments, the artificial-reality engine 134 receives information from the sensors 114 on the head-mounted display 110 and provides the information to an artificial-reality application 132. Based on the received information, the artificial-reality engine 134 determines media content to provide to the head-mounted display 110 for presentation to the user via the electronic display 112 and/or a type of haptic feedback to be created by the haptic-feedback mechanism 122 of the wearable device 120. For example, if the artificial-reality engine 134 receives information from the sensors 114 on the head-mounted display 110 indicating that the user has looked to the left, the artificial-reality engine 134 generates content for the head-mounted display 110 that mirrors the user's movement in a virtual environment.

Similarly, in some embodiments, the artificial-reality engine 134 receives information from the sensors 124 on the wearable device 120 and provides the information to an artificial-reality application 132. The application 132 can use the information to perform an action within the artificial world of the application 132. For example, if the artificial-reality engine 134 receives information from the sensors 124 that the user has closed his fingers around a position corresponding to a coffee mug in the artificial environment and raised his hand, a simulated hand in the artificial-reality application 132 picks up the artificial coffee mug and lifts it to a corresponding height. As noted above, the information received by the artificial-reality engine 134 can also include information from the head-mounted display 110. For example, cameras on the head-mounted display 110 may capture movements of the wearable device 120, and the application 132 can use this additional information to perform the action within the artificial world of the application 132.

In some embodiments, the artificial-reality engine 134 provides feedback to the user that the action was performed. The provided feedback may be visual via the electronic display 112 in the head-mounted display 110 (e.g., displaying the simulated hand as it picks up and lifts the virtual coffee mug) and/or haptic feedback via the haptic-feedback mechanism 122 in the wearable device 120. For example, the haptic feedback may vibrate in a certain way to simulate the sensation of firing a firearm in an artificial-reality video game. To do this, the wearable device 120 changes (either directly or indirectly) fluid pressure of one or more of bladders of the haptic-feedback mechanism 122. When inflated by a threshold amount (and/or inflated at a threshold frequency, such as at least 5 Hz), a respective bladder of the haptic-feedback mechanism 122 presses against the user's body, resulting in the haptic feedback.

In another example, the haptic-feedback mechanism 122 may inhibit movement of the user's fingers from curling past a certain point to simulate, e.g., the sensation of touching a solid coffee mug. To do this, the wearable device 120 changes (either directly or indirectly) a pressurized state (i.e., inflates) of two or more bladders 204 (or a single bladder that includes multiple pockets). Once inflated, the two or more bladders 204 are configured to interfere with each other (i.e., press or push against each other) when the user attempts to curl his fingers. Interference of the bladders (or their respective pockets) creates forces on the finger phalanges, as one example, in a direction very similar to the forces induced by physical objects during natural hand-object interaction (i.e., simulate the forces that would actually be felt by a user when he or she touches (and lifts) a solid coffee mug in the real world).

In view of the examples above, the wearable device 120 is used to further immerse the user in artificial-reality experience such that the user not only sees (at least in some instances) the data on the head-mounted display 110, but the user may also "feel" certain aspects of the displayed data. Moreover, the wearable device 120 is designed to limit encumbrances imposed onto the user, at least when encumbrances are not desired.

To provide some additional context, the bladders described herein are configured to transition between a first pressurized state and a second pressurized state to provide haptic feedback to the user. Due to the ever-changing nature of virtual and augmented reality, the bladders may be required to transition between the two states hundreds, or perhaps thousands of times, during a single use. Thus, the bladders described herein are durable and designed to quickly transition from state to state (e.g., within 10 milliseconds). In the first pressurized state, a respective bladder is unpressurized (or a fluid pressure inside the respective bladder is below a threshold pressure) and does not provide haptic feedback to a portion of the wearer's body. However, once in the second pressurized state (e.g., the fluid pressure inside the respective bladder reaches the threshold pressure), the respective bladder is configured to expand, and in some cases, resist movement of the portion of the wearer's body.

Figure 2:
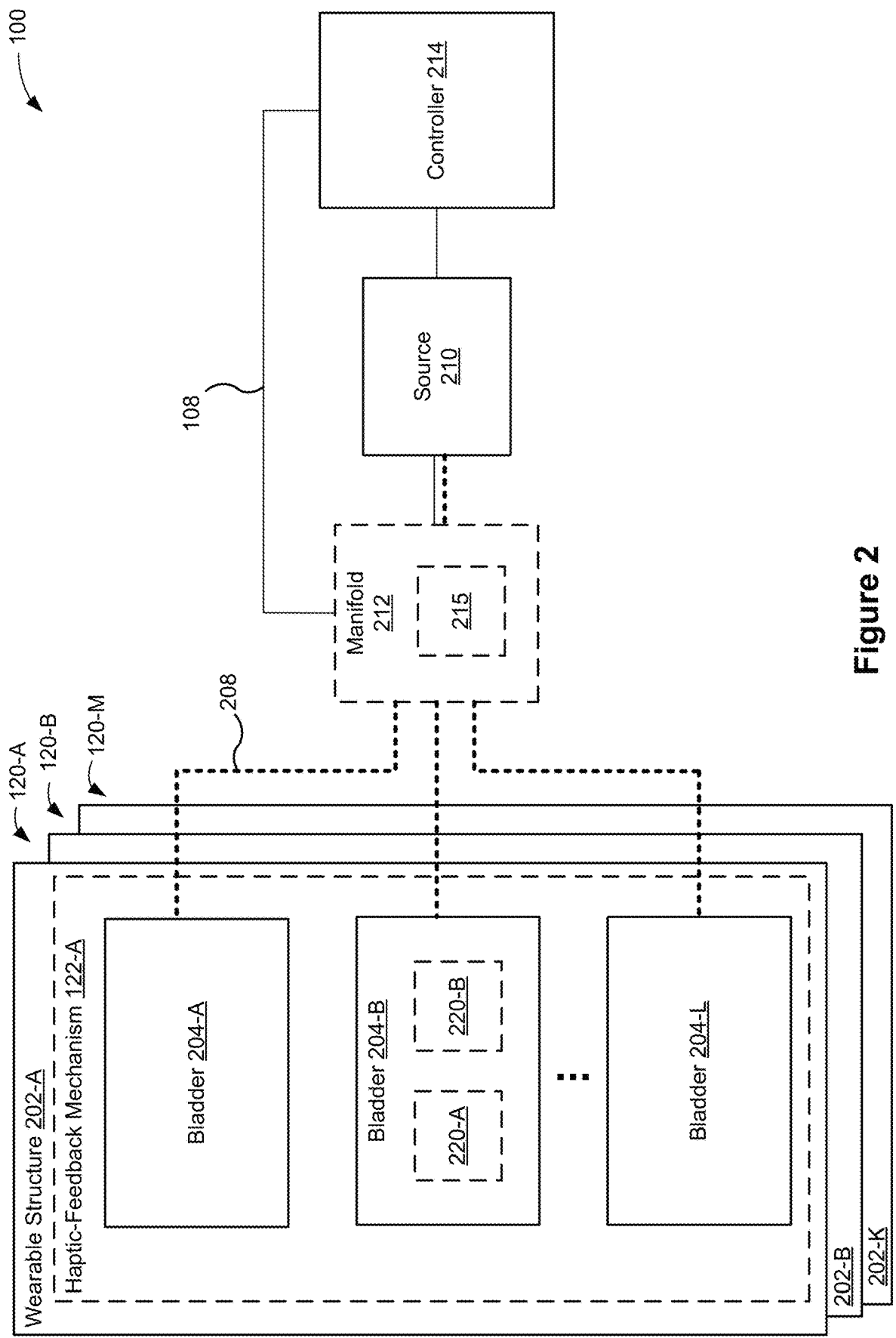
FIG. 2 is a schematic of an example haptics system in accordance with some embodiments.

FIG. 2 is a schematic of the system 100 in accordance with some embodiments. The components in FIG. 2 are illustrated in a particular arrangement for ease of illustration and one skilled in the art will appreciate that other arrangements are possible. Moreover, while some example features are illustrated, various other features have not been illustrated for the sake of brevity and so as not to obscure pertinent aspects of the example implementations disclosed herein.

As a non-limiting example, the system 100 includes a plurality of wearable devices 120-A, 120-B, ... 120-M, each of which includes a wearable structure 202 and a haptic-feedback mechanism 122. Each haptic-feedback mechanism 122 includes one or more bladders 204, and as explained above, the one or more bladders 204 are configured to provide haptic stimulations to a wearer of the wearable device 120. The wearable structure 202 of each wearable device 120 can be various articles of clothing (e.g., gloves, socks, shirts, or pants) or other wearable structure (e.g., watch band), and thus, the user may wear multiple wearable devices 120 that provide haptic stimulations to different parts of the body. In some embodiments, the wearable structure 202 is made from an elastic material, thereby allowing the wearable device 120 to fit various users.

Each bladder 204 is integrated with (e.g., embedded in or coupled to) the wearable structure 202. The bladder 204 is a sealed, inflatable pocket made from a durable, puncture resistance material (at least partially), such as thermoplastic polyurethane (TPU) or the like. Each bladder 204 is configured to expand or contract according to fluid pressure within each bladder. Fluid as used herein can be various media, including air, an inert gas, or a liquid. In some embodiments, each bladder 204 delivers (e.g., imparts) a haptic stimulation to the user wearing the wearable structure 202 when the bladder expands a threshold amount (i.e., a fluid pressure within the bladder reaches a threshold pressure). The threshold amount of expansion can range from 1 mm to 15 mm. In some embodiments, each bladder 204 can also deliver a haptic stimulation to the user wearing the wearable structure 202 when the bladder expands and contracts at a threshold frequency (e.g., greater than approximately 5 Hz).

In other embodiments, two or more neighboring bladders 204 deliver a haptic stimulation to the user wearing the wearable structure 202 when the bladders each expand a threshold amount (i.e., a fluid pressure within the bladder reaches a threshold pressure). In these embodiments, the haptic stimulation may be imparted onto the user upon expansion of the bladders 204, and/or when the user moves the portion of his or her body where the bladders 204 are coupled to (e.g., user attempts to curl his or her finger when the bladders 204 are positioned adjacent to a palmer surface of the user's finger). When the user moves, the two or more neighboring bladders 204 interfere with each other, thereby preventing the user from any further movement.

In some embodiments, a single bladder 204 includes two or more pockets 220-A, 220-B that are configured to expand and contract according to a fluid pressure inside the inflatable bladder 204. Furthermore, the two or more pockets 220-A, 220-B are configured to deliver a haptic stimulation to the user wearing the wearable structure 202 when a fluid pressure within the bladder 204 reaches a threshold pressure. Like the previous embodiments, when the user moves, the two or more two or more pockets 220-A, 220-B interfere with each other, thereby preventing the user from any further movement.

The system 100 also includes a controller 214 and a fluid source 210 (e.g., a pneumatic device). In some embodiments, the controller 214 is part of the computer system 130 (e.g., the processor of the computer system 130). Alternatively, in some embodiments, the controller 214 is part of the wearable device 120. The controller 214 is configured to control operation of the source 210, and in turn the operation (at least partially) of the wearable devices 120. For example, the controller 214 sends one or more signals to the source 210 to activate the source 210 (e.g., turn it on and off). The one or more signals may specify a desired pressure (e.g., 0.5 to 40 pounds-per-square inch, PSI) to be output by the source 210. Additionally, the one or more signals may specify a desired frequency for outputting the desired pressure (e.g., 0.5 Hz to 50 Hz). The one or more signals may further specify one or more of: (i) one or more target bladders 204 to be inflated and (ii) a pattern of inflation for the one or more target bladders 204.

Generation of the one or more signals, and in turn the pressure output by the source 210, may be based on information collected by the HMD sensors 114 and/or the wearable device sensors 124. For example, the one or more signals may cause the source 210 to increase the pressure inside one or more bladders 204 of a first wearable device 120 at a first time, based on the information collected by the sensors 114 and/or the sensors 124 (e.g., the user makes contact with the virtual coffee mug or fires a virtual firearm). Then, the controller 214 may send one or more additional signals to the source 210 that cause the source 210 to further increase the pressure inside the one or more bladders 204 of the first wearable device 120 at a second time after the first time, based on additional information collected by the sensors 114 and/or the sensors 124 (e.g., the user grasps and lifts the virtual coffee mug). Further, the one or more signals may cause the source 210 to inflate one or more bladders 204 in a first wearable device 120-A, while one or more bladders 204 in a second wearable device 120-B remain unchanged (or are inflated to some other pressure). Additionally, the one or more signals may cause the source 210 to inflate one or more bladders 204 in the first wearable device 120-A to a first pressure and inflate one or more other bladders 204 in the first wearable device 120-A to a second pressure different from the first pressure. Depending on the number of wearable devices 120 serviced by the source 210, and the number of bladders 204 therein, many different inflation configurations can be achieved through the one or more signals and the examples above are not meant to be limiting.

In some embodiments, the system 100 includes a manifold 212 between the source 210 and the wearable devices 120. In some embodiments, the manifold 212 includes one or more valves (not shown) that fluidically (e.g., pneumatically) couple each of the haptic-feedback mechanisms 122 with the source 210 via tubing 208 (also referred to herein as "conduits"). In some embodiments, the tubing is ethylene propylene diene monomer (EPDM) rubber tubing with 1/32" inner diameter (various other tubing can also be used). In some embodiments, the manifold 212 is in communication with the controller 214, and the controller 214 controls the one or more valves of the manifold 212 (e.g., the controller generates one or more control signals). The manifold 212 is configured to switchably couple the source 210 with the bladders 204 of the same or different wearable devices 120 based on one or more control signals from the controller 214. In some embodiments, instead of the manifold 212 being used to fluidically couple the source 210 with the haptic-feedback mechanisms 122, the system 100 includes multiple sources 210, where each is fluidically coupled directly with a single (or multiple) bladder(s) 204. In some embodiments, the source 210 and the optional manifold 212 are configured as part of one or more of the wearable devices 120 (not illustrated) while, in other embodiments, the source 210 and the optional manifold 212 are configured as external to the wearable device 120. A single source 210 may be shared by multiple wearable devices 120.

In some embodiments, the manifold 212 includes one or more back-flow valves 215 that is configured to selectively open and close to regulate fluid flow between the manifold 212 from the bladders 204. When closed, the one or more back-flow valves 215 stop fluid flowing from the bladders 204 back to the manifold 212. In some other embodiments, the one or more back-flow valves 215 are distinct components separate from the manifold 212.

In some embodiments, the source 210 is a pneumatic device, hydraulic device, a pneudraulic device, or some other device capable of adding and removing a medium from the one or more bladders 204. In other words, the discussion herein is not limited to pneumatic devices, but for ease of discussion, pneumatic devices are used as the primary example in the discussion below.

The devices shown in FIG. 2 may be coupled via a wired connection (e.g., via busing 108). Alternatively, one or more of the devices shown in FIG. 2 may be wirelessly connected (e.g., via short-range communication signals).

Various embodiments of the haptic-feedback mechanism 122 are illustrated and described below. For example, a first embodiment of the haptic-feedback mechanism 122 is illustrated and described with reference to FIGS. 3A-3E. A second embodiment of the haptic-feedback mechanism 122 is illustrated and described with reference to FIGS. 6A-6D. A third embodiment of the haptic-feedback mechanism 122 is illustrated and described with reference to FIG. 7A-7E. A fourth embodiment of the haptic-feedback mechanism 122 is illustrated and described with reference to FIG. 8A-8C. Note that while the embodiments of the haptic-feedback mechanism 122 are discussed separately, in some embodiments, a representative wearable device 120 may include one or more of the embodiments discussed below.

First Embodiment—Inflatable Bladders with Texturized Surfaces

Figure 3A:
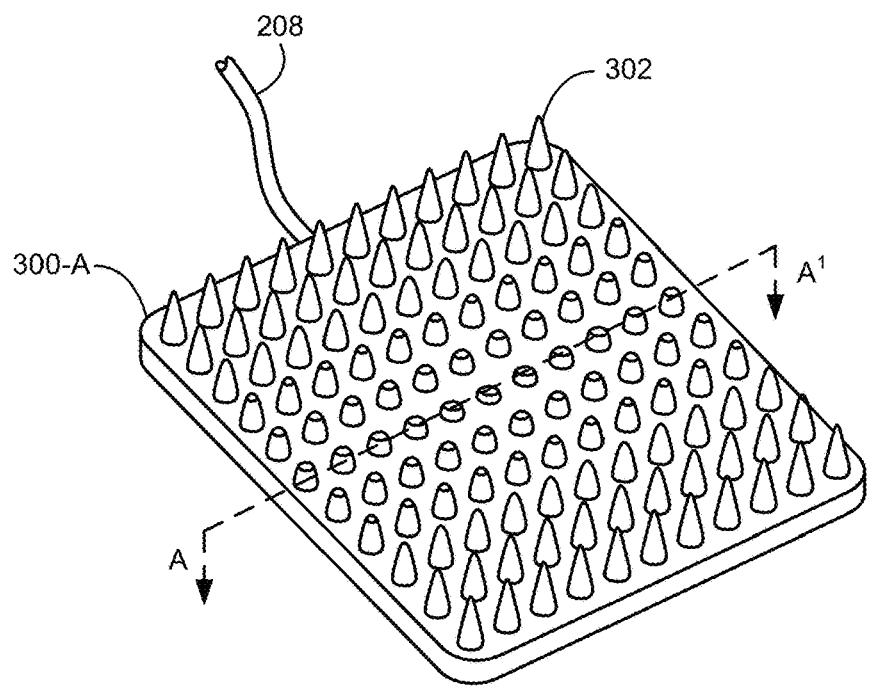
FIGS. 3A and 3B show example inflatable bladders in an unpressurized state in accordance with some embodiments.
Figure 3B:
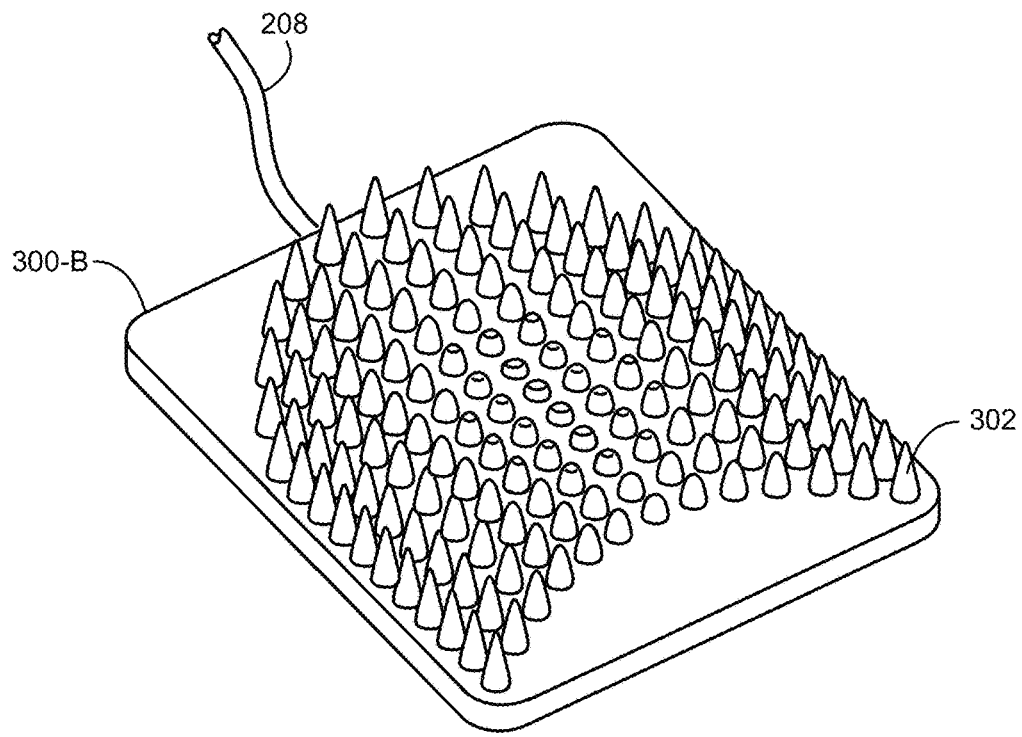

FIGS. 3A and 3B show example inflatable bladders 300 in an unpressurized state in accordance with some embodiments. In particular, FIG. 3A shows a first example inflatable bladder 300-A that includes a plurality of barbs 302 arranged in a first pattern while FIG. 3B shows a second example inflatable bladder 300-B that includes a plurality of barbs 302 arranged in a second pattern different from the first pattern. The inflatable bladders 300 in FIGS. 3A and 3B are examples of the inflatable bladders 204 discussed above with reference to FIG. 2.

The inflatable bladders 300-A, 300-B are configured to be coupled to (or otherwise integrated with) a wearable structure 202 and also interact with a user's body at a target location. To illustrate, if the target location on the user's body is the proximal interphalangeal joint of the user's right index finger (palmer side), then the inflatable bladder 300 is coupled to the wearable structure 202 (e.g., glove) at a location that allows the inflatable bladder 300 to interact with the user's body at the target location (i.e., the inflatable bladder 300 is coupled to the wearable structure 202 one-third of the way up the portion of the wearable structure 202 configured to receive the user's right index finger). Each bladder 300 is configured to expand and contract according to fluid pressure within each bladder 204. Furthermore, each bladder 300 delivers (e.g., imparts) a haptic stimulation to the user wearing the wearable structure 202 when the bladder 300 expands a threshold amount (and/or vibrates at a threshold frequency), as shown in FIG. 3E.

As mentioned above, each bladder 300 includes a plurality of barbs 302. The plurality of barbs 302 may be integrally formed with the bladder 300 or may be attached to a surface of the bladder 300. The plurality of barbs 302 may be made from the same material or a different material than the material of the surface of the bladder 300. When the inflatable bladder 300 is coupled to the wearable structure 202 and the wearable structure 202 is donned by a user, the plurality of barbs 302 are positioned adjacent to (e.g., facing) the user's body. In other words, the plurality of barbs 302 are configured to press against or otherwise interact with the user's body when the wearable device 120 is worn. As will be discussed in more detailed below with respect to FIG. 3E, the plurality of barbs 302 are configured to protrude from a surface of the inflatable bladder 300 (e.g., like the spikes of a pufferfish) in response to the inflatable bladder 300 receiving fluid from the source 210. Accordingly, not only does the user feel the expansion of the bladder 300, but the user also feels a distinct interaction caused by the protruding barbs 302 (FIG. 3E) pressing against the user's body.

In some embodiments, the plurality of barbs 302 are arranged in a uniform pattern, such that the barbs 302 are equally spaced from one another and each barb 302 has the same (or substantially similar) shape. In some other embodiments, the plurality of barbs 302 are arranged in a non-uniform pattern, such that the barbs 302 may have different shapes and/or spacings. A pattern (uniform or non-uniform) of the plurality of barbs 302 can be defined according to a profile of the user's body at the target location. For example, if the target location is a palmer surface of the user's index finger, then the pattern of the plurality of barbs 302 may be defined according to a profile of the palmer surface of the user's finger. In another example, if the target location is a palmer surface of the user's right thumb, then the pattern of the plurality of barbs 302 may be defined according to a profile of the palmer surface of user's right thumb, which may or may not differ from the pattern of the plurality of barbs 302 that is defined according to the profile of the palmer surface of the user's finger.

In FIG. 3A, the plurality of barbs 302 have a first pattern that is defined based on a palmer surface of a phalange of a human finger or thumb (e.g., the intermediate phalange of an index finger). As shown, edge barbs 302 of the inflatable bladder 300-A are longer and more pointed relative to middle/central barbs 302 of the inflatable bladder 300-A, which appear blunted. In FIG. 3B, the plurality of barbs 302 have a second pattern, different from the first pattern, that is defined based on a palmer surface of a phalange of a human finger or thumb. As shown, the plurality of barbs 302 do not occupy the entire surface of the inflatable bladder 300-B but rather form a unique shape that is tailored to a shape of the phalange of the human finger or thumb. Furthermore, edge barbs 302 of the inflatable bladder 300-B are longer and more pointed relative to middle/central barbs 302 of the inflatable bladder 300-B, which are again blunted.

Differences between the edge barbs 302 and the middle/central barbs 302, and a generally layout of the barbs 302 in FIGS. 3A and 3B, may be made based on the ability of that portion of the user's body (e.g., the thumb) to sense touch. It is noted that the pattern of the plurality of barbs 302 is not limited to fingers and thumbs, but rather the pattern of the plurality of barbs 302 may be tailored to any portion of a person's body. The ability to tailor a pattern of the barbs 302 is particularly useful in haptic devices because different portions of the human body have different touch-sensory capabilities (e.g., different profiles/shapes with unique touch sensing capacities). Consequently, the pattern of the barbs 302 can be selected/designed to leverage and maximize the sensory capabilities at a particular portion of the body. The patterns shown in FIGS. 3A and 3B are merely two possible examples for two parts of the human body, and various other designs could also be used on the discussed portions of the body.

Figure 3C:
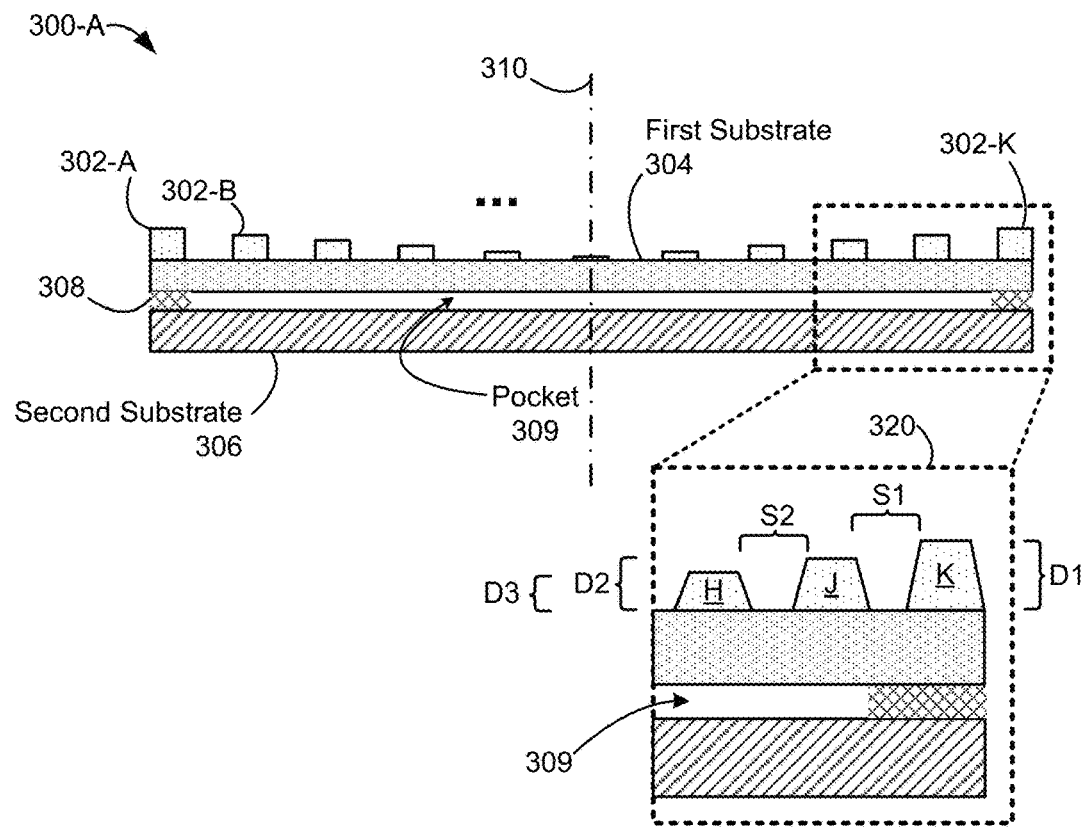
FIGS. 3C and 3D show cross-sectional views of the inflatable bladder (taken along line A-A$^1$ in FIG. 3A).
Figure 3D:
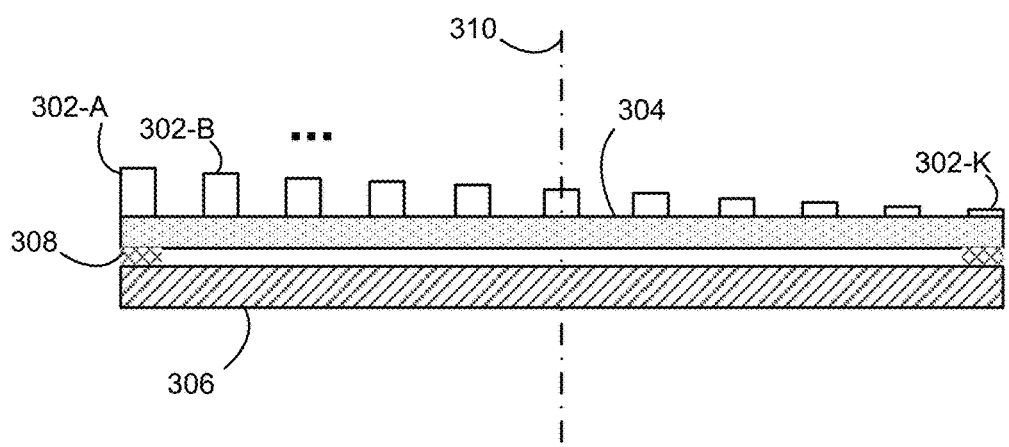
Figure 3E:
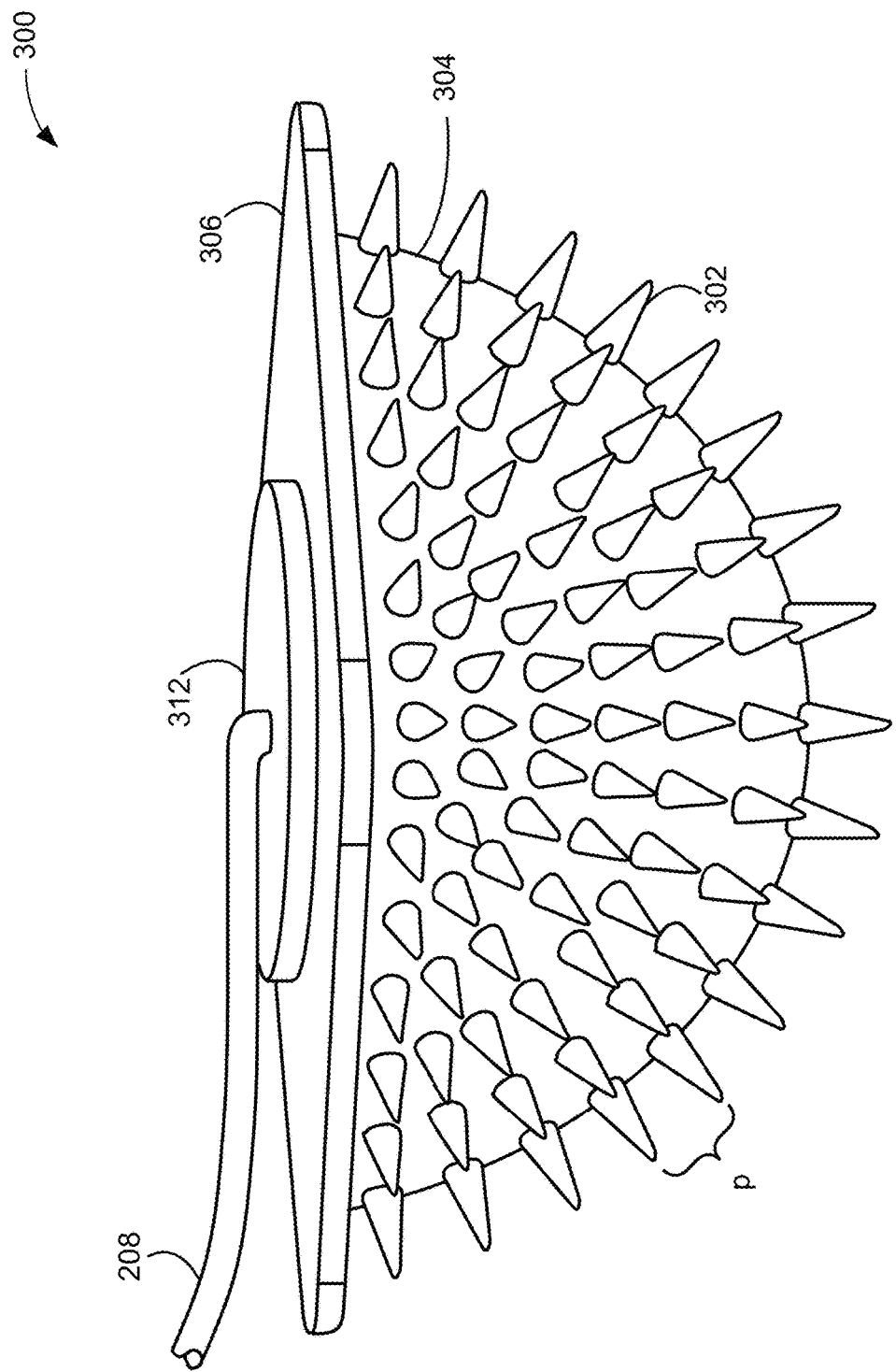
FIG. 3E shows an example inflatable bladder in a pressurized state in accordance with some embodiments.

FIG. 3C shows a cross-sectional view of the inflatable bladder 300-A (taken along line A-A[1] in FIG. 3A), while FIG. 3D shows an alternative cross-sectional view of an example inflatable bladder 300.

In FIG. 3C, the inflatable bladder 300-A includes a first substrate 304 and a second substrate 306 coupled to the first substrate 304 by an adhesive 308. In some instances, the first substrate 304 is generally referred to as the "first surface" while the second substrate 306 is generally referred to as the "second surface." In this particular example, the adhesive 308 is positioned along respective edges of the first substrate 304 and the second substrate 306, which allows for a large pocket 309 to be formed between the first substrate 304 and the second substrate 306. A size of the pocket 309 can be reduced by adhering (via the adhesive 308) a larger portion of the respective edges together. Likewise, a size of the pocket 309 can be increased by adhering (via the adhesive 308) a lesser portion of the respective edges together. Notably, the first substrate 304 is made from an elastic material (e.g., TPU or the like) while the second substrate 306 is made from an inelastic material (e.g., fiberglass reinforced textile or the like). In this configuration, the first substrate 304 bulges away from the second substrate 306, at least partially, when a fluid is received in the pocket 309 (e.g., the source 210 adds fluid to the inflatable bladder 300 to pressurize the pocket 309), as shown in FIG. 3E. The degree at which the first substrate 304 bulges is related to, at least partially, a size of the pocket 309 (e.g., a larger pocket 309 allows for the first substrate 304 to bulge significantly).

As also shown in FIG. 3C, the plurality of barbs 302-A, 302-B, . . . , 302-K of the bladder 300-A are positioned on a surface of the first substrate 304. FIG. 3C illustrates how a height of the barbs 302 can change across a width of the first substrate 304. Furthermore, in this particular example, the plurality of barbs 302-A, 302-B, . . . 302-K are symmetrical about line 310. In other embodiments, such as the embodiment shown in FIG. 3D, the plurality of barbs 302-A, 302-B, . . . 302-K are not symmetric. In some embodiments, the plurality of barbs 302-A, 302-B, . . . 302-K are symmetric in a first direction (e.g., laterally) while other barbs 302 are not symmetric in a second direction (e.g., longitudinally), or vice versa.

The magnified view 320 in FIG. 3C provides additional detail for the plurality of barbs 302-A, 302-B, . . . 302-K. Note that while the magnified view 320 only shows a subset of the plurality of barbs 302, the discussion below may equally apply to all the barbs in the plurality of barbs 302. As shown, the barbs 302-H, 302-J, 302-K have a polygonal shape when the inflatable bladder 300-A is in an unpressurized state. The polygonal shape of the barbs 302 shown in the magnified view 320 can promote a desired shape when the inflatable bladder 300-A is in a pressurized state, such as the spike shape of the barbs 302 shown in FIG. 3E. In some embodiments, respective shapes of the barbs in the plurality of barbs 302-A, 302-B, . . . 302-K are also defined according to the profile of the user's body at the target location. In other words, the polygonal shape of the barbs 302 shown in the magnified view 320 is selected based on the profile of the user's body. While not shown, in some embodiments, the barbs in the plurality of barbs 302-A, 302-B, . . . 302-K each has a polygonal shape, while in other embodiments, one or more barbs in the plurality of barbs 302-A, 302-B, . . . 302-K do not have the polygonal shape.

The magnified view 320 also shows that barb 302-K is separated from barb 302-J by a first distance (S1) while barb 302-J is separated from barb 302-H by a second distance (S2). In some embodiments, the first distance (S1) is the same as the second distance (S2), while in other embodiments, the first distance (S1) is different from the second distance (S2). Like barb shape, distances separating neighboring barbs 302 in the plurality of barbs 302-A, 302-B, . . . 302-K may be defined according to the profile of the user's body at the target location. As one example, each of the barbs 302 in the plurality of barbs 302-A, 302-B, . . . 302-K may be separated by the first distance (S1), the second distance (S2), some combination thereof, or some other distance(s). Note that distances separating neighboring barbs 302 may differ substantially from one body part to the next. For example, when the target location is on the user's finger, neighboring barbs 302 may be separated by first distances (e.g., approximately 1 mm) while, when the target location is on the user's leg, neighboring barbs 302 may be separated by second distances (e.g., approximately 5 mm).

The magnified view 320 also shows depths (D1, D2, D3) of the barbs 302-H, 302-J, 302-K. In some embodiments, respective depths of the barbs in the plurality of barbs 302-A, 302-B, . . . 302-K are also defined according to the profile of the user's body at the target location. Like a shape of the barbs 302, a depth (and width) of the barbs 302 is another factor that can be used to promote a spiked shape of the barbs 302 when the inflatable bladder 300-A is in a pressurized state. Also, depths of the barbs 302 may differ substantially from one body part to the next.

It is noted that a roughness (bumpiness, coarseness) of the first surface 304 of a respective inflatable bladder 300 increases with fluid pressure inside the inflatable bladder 300. For example, in FIGS. 3C and 3D, the inflatable bladder 300 is unpressurized (or is at a low pressure) and, consequently, the first surface 304 of the inflatable bladder 300 is fairly smooth (i.e., low roughness). In contrast, in FIG. 3E, the inflatable bladder 300 is pressurized and, consequently, the first surface 304 of the inflatable bladder 300 is rough. Moreover, the inflatable bladder 300 may have a maximum pressure (e.g., fluid pressure inside the bladder 300 cannot exceed some maximum pressure). In such instances, the first surface 304 of the inflatable bladder 300 is configured to have a maximum roughness when the fluid pressure inside the inflatable bladder 300 reaches the maximum pressure. To provide some context, the maximum pressure may be around 35 PSI. It is also noted that fluid pressures ranging from 5 to 20 PSI (preferably 10-15 PSI) delivered high quality haptic feedback.

FIG. 3E shows the example inflatable bladder 300 in a pressurized state in accordance with some embodiments. As shown, the plurality of barbs 302 of the inflatable bladder 300 are protruding from the first surface 304 in response to the inflatable bladder 300 receiving fluid from the source 210. When the wearable device 120 is donned by a user, the plurality of barbs 302 are configured to interact with the user's body at a target location (i.e., impart a haptic stimulation to the user's body at the target location in response to the inflatable bladder receiving the fluid from the source). The inflatable bladder 300 in FIG. 3E may be pressurized to the maximum pressure.

When the inflatable bladder 300 is in the pressurized state, first distances (p) separate the barbs in the plurality of barbs 302 (more specifically, the first distances separate tips of the plurality of barbs 302). The first distances (p) separating the barbs in the plurality of barbs 302 may be the same or different across the plurality of barbs 302. For example, a first group of barbs 302 may be separated by lesser distances (p) compared to distances (p) separating a second group of barbs 302. In this example, the first group of barbs 302 may form a tight cluster of barbs 302, which may be needed to impart a sufficient haptic stimulation to a particular portion of the user's body. Note that distances (p) separating the tips of the plurality of barbs 302 increases when the inflatable bladder 300 transitions from the unpressurized state to the pressurized state.

In some embodiments, the first surface 304 of the inflatable bladder 300 transitions from a concave shape to a convex shape in response to the inflatable bladder 300 receiving the fluid from the source 210. For example, in FIG. 3E, the first surface 304 of the inflatable bladder 300 has a convex shape when pressurized. When unpressurized, the first surface 304 (and potentially the second surface 306) may have a concave shape that fits (i.e., complements) a profile of the user's body at the target location (e.g., fits a curvature of a user's finger). Also, the convex shape of the first surface 304 may cause (or otherwise promote) the plurality of barbs 302 to protrude from the first surface 304.

Figure 4:
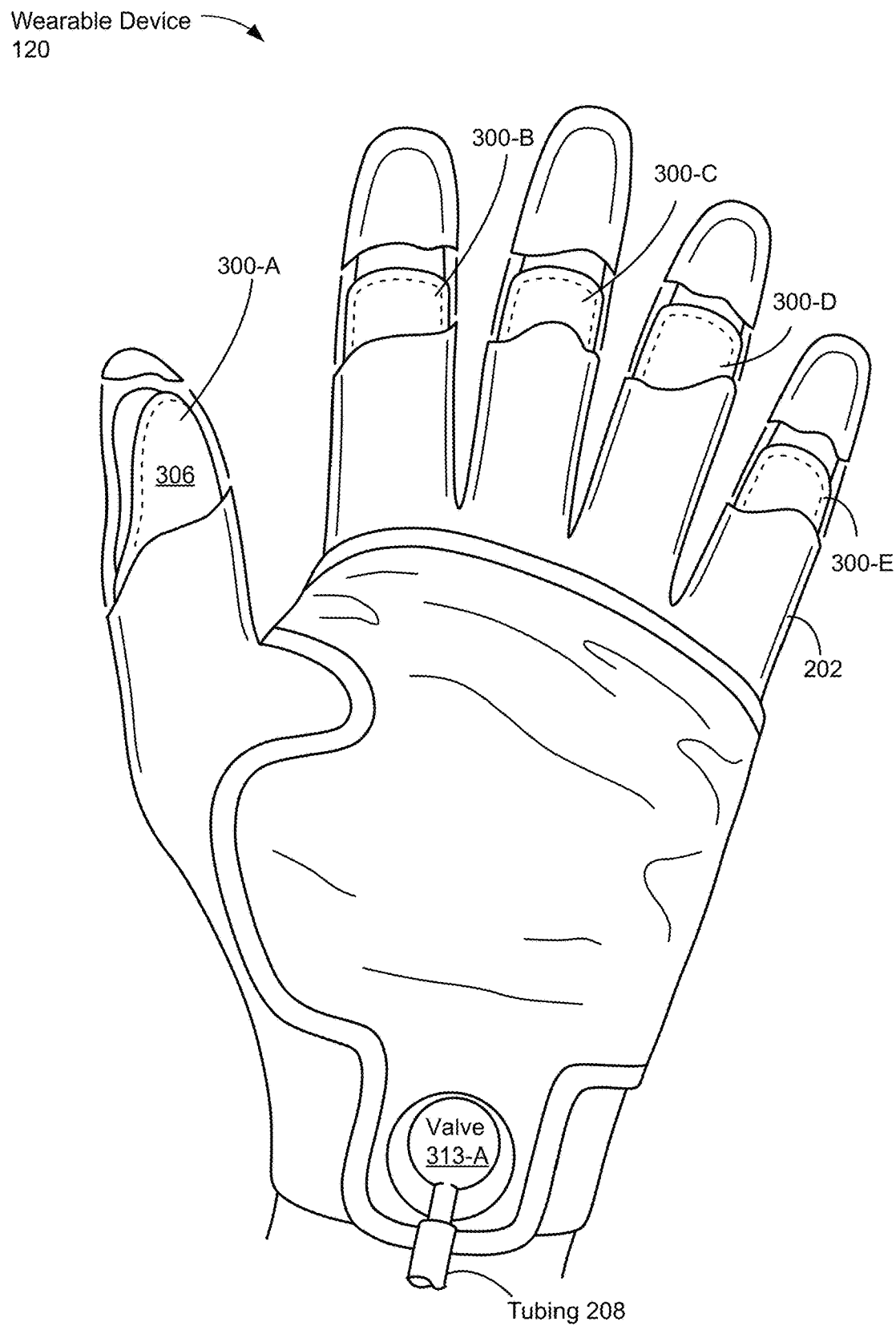
FIG. 4 shows an example wearable device with a plurality of inflatable bladders in accordance with some embodiments.

FIG. 4 shows an example wearable device 120 with a plurality of inflatable bladders 300-A-300-E in accordance with some embodiments. For ease of illustration, portions of the wearable structure 202 have been removed from FIG. 4 to show the inflatable bladders 300-A-300-E hidden beneath.

As shown in FIG. 4, an inflatable bladder 300-A is positioned on a palmer region of the user's thumb, while inflatable bladders 300-B-300-E are positioned on palmar portions of the user's fingers. In such a configuration, each of these regions of the user's body can experience one or more haptic stimulations. In some embodiments, the inflatable bladders 300-A-300-E include different patterns of barbs 302. Note that the barbs 302 are not shown in FIG. 4 because they are facing the user's body. The second surface 306 of the inflatable bladders 300-A-300-E, however, is shown in FIG. 4 as this is the surface of the inflatable bladders 300-A-300-E that faces away from the user's body.

In the illustrated embodiments, the inflatable bladders 300-A-300-E are serviced by a single valve 313-A (i.e., the bladders 300 are fluidically coupled to the source 210 by a single conduit 208), and as a result, the inflatable bladders 300-A-300-E are inflated and deflated together. While not shown, in some embodiments, the inflatable bladders 300-A-300-E are serviced by distinct valves 313 (i.e., the bladders 300 are fluidically coupled to the source 210 by distinct conduits 208). Either way, when the bladders 300 are unpressurized, each of the bladders 300 are flexible, and when the bladders 300 are pressurized, each of the bladders 300 is less flexible (i.e., semi-rigid or rigid).

The second and third embodiments discussed below are both directed towards haptic-feedback mechanisms 122 that use interference to impart haptic stimulations onto a user. In particular, the haptic-feedback mechanisms 122 in these embodiments include at least one inflatable bladder 204 that has two or more pockets 220 configured to, when inflated, impart one or more directional forces onto the user at a target location (e.g., a finger joint) that impede movement of a portion of the user's body (e.g., a user's finger). Importantly, the one or more directional forces are caused by the two or more pockets 220 interfering with each other when inflated, as shown in FIG. 5D (discussed below). Stated differently, in the embodiments discussed below, pockets of bladders interfere when inflated to render impedance and torque at a target location, such as a finger joint. Using the finger joint as an illustrative example, interference of the pockets creates forces on the finger phalanges in a direction very similar to the forces induced by physical objects during natural hand-object interaction, making the designs of the second and third embodiments perceptually appealing. As explained above with reference to FIG. 2, each inflatable bladder 204 is coupled to a wearable structure 202, which is not shown in most of the figures below for ease of discussion and illustration.

Figure 5A:
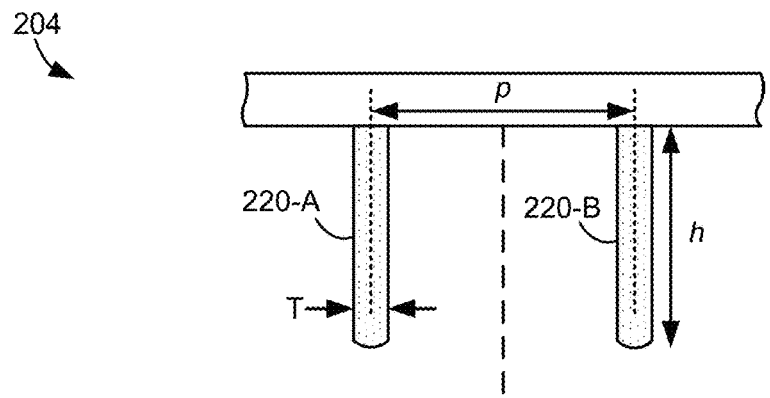
FIG. 5A shows a simplified inflatable bladder that includes multiple pockets in an unpressurized state in accordance with some embodiments.
Figure 5B:
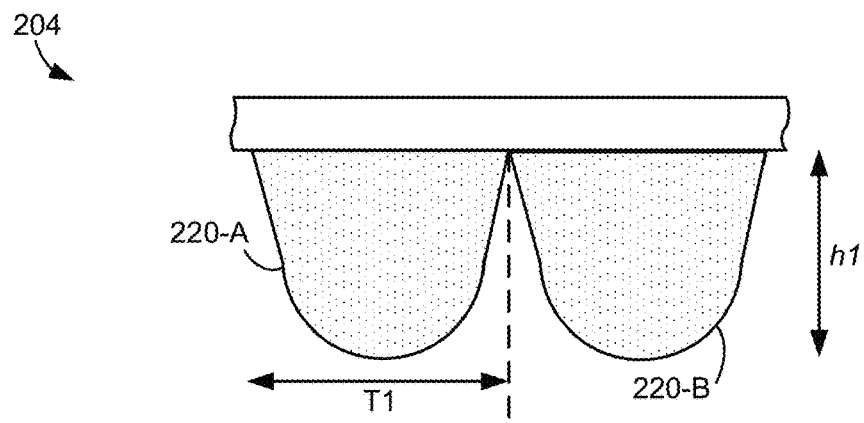
FIG. 5B shows the simplified inflatable bladder of FIG. 5A in a pressurized state in accordance with some embodiments.
Figure 5C:
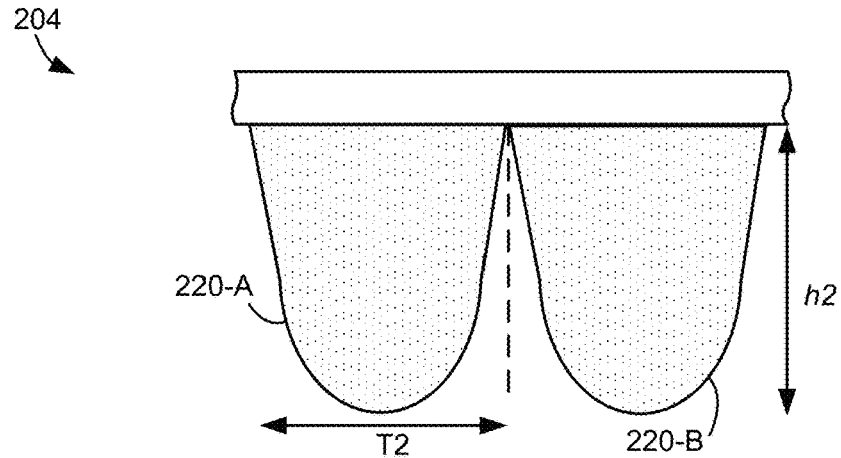
FIG. 5C shows the simplified inflatable bladder of FIG. 5A in a different pressurized state in accordance with some embodiments.
Figure 5D:
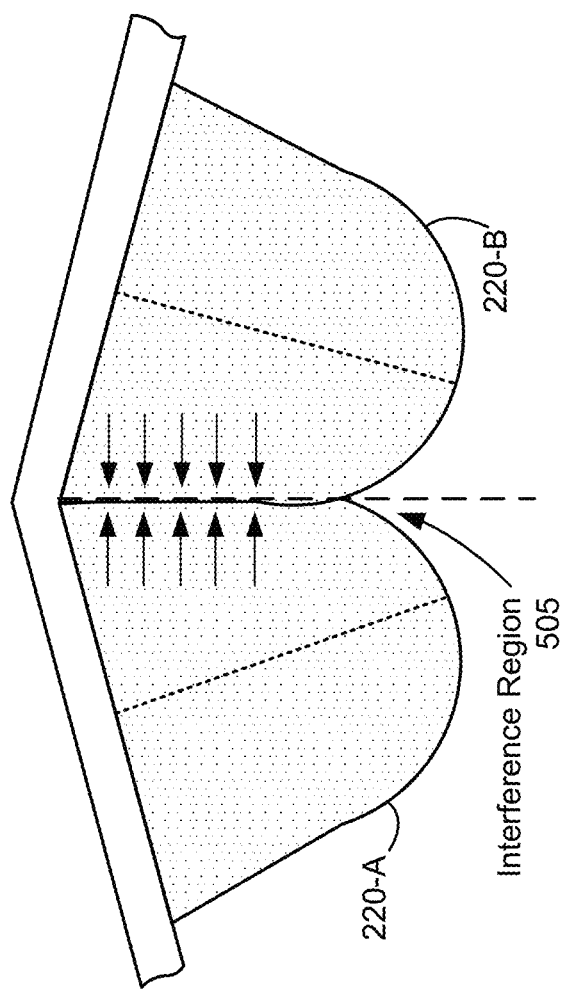
FIG. 5D shows the multiple pockets interfering with each other, in accordance with some embodiments.

FIGS. 5A-5D are included herein to provide some context to the discussion of the second and third embodiments. To begin, FIG. 5A shows a simplified inflatable bladder 204, in an unpressurized state, that includes a first pocket 220-A and a second pocket 220-B. As shown in FIG. 5A, the first pocket 220-A is separated from the second pocket 220-B by a separation distance (p), and each pocket 220 has a height (h) and a thickness (T). As will be discussed in more detail, the inflatable bladders 204 discussed with reference to the second and third embodiments may include any number of pockets 220.

In the unpressurized state of FIG. 5A, the first pocket 220-A and the second pocket 220-B are deflated, and, thus, they do not interact with each other. For example, if the bladder 204 is positioned on a user's finger, the first pocket 220-A and the second pocket 220-B will not impede finger flexion (e.g., the user is free to bend or otherwise curl his or her finger). This result is achieved because the inflatable bladder 204 as a whole is made from flexible materials designed/selected to not encumber movement of the user's body when the inflatable bladder 204 is unpressurized. It is also noted that the inflatable bladder 204 may include two main components: (i) the first pocket 220-A and the second pocket 220-B (made from the elastic material) and (ii) a substrate (made from an inelastic, yet flexible, material) coupled with the first pocket 220-A and the second pocket 220-B. A design of the inflatable bladder 204 is discussed in further detail below with reference to FIGS. 6A-6D and 7A-7E.

FIGS. 5B and 5C show the simplified inflatable bladder 204 from FIG. 5A in a pressurized state (i.e., inflated). In the pressurized state of FIGS. 5B and 5C, the first pocket 220-A and the second pocket 220-B are inflated, and, thus, they are positioned to interact with each other. Notably, in FIG. 5B, the first pocket 220-A and the second pocket 220-B have expanded to a first height (h1) and a first thickness (T1), while in FIG. 5C, the first pocket 220-A and the second pocket 220-B have expanded to a second height (h2) and a second thickness (T2). The differences in height and thickness in FIGS. 5B and 5C can be attributed to characteristics of the pockets 220-A, 220-B themselves, such as material choice and sidewall thickness. For example, pockets 220 tend to elongate further when a thickness of their sidewalls is reduced from some baseline thickness. Additionally, a pressure inside the first pocket 220-A and the second pocket 220-B in FIG. 5B may be lower than a pressure inside the first pocket 220-A and the second pocket 220-B in FIG. 5C (which may also explain why the second height (h2) is greater than the first height (h1)).

FIG. 5D shows the first pocket 220-A and the second pocket 220-B interfering with each other at the interference region 505. When the first pocket 220-A and the second pocket 220-B interfere with each other (e.g., as a result of the user attempting to curl his or her finger when the inflatable bladder 204 is in the pressurized state), forces are created in directions that are opposite to the arrows shown in FIG. 5D, and these forces are resist movement of the user's body. As such, if the inflatable bladder 204 is positioned at a joint on the user's body (e.g., a joint separating finger phalanges), the first pocket 220-A and the second pocket 220-B prevent the user from bending his or her finger further at the joint (e.g., the user is prevented from curling his or her finger past a certain point). Accordingly, the second and third embodiments discussed below provide innovative mechanisms that can be used to prevent a user from moving (e.g., bending) certain portions of his or her body. Furthermore, the second and third embodiments implement designs that can be easily incorporated into garments (e.g., glovers, shirts, socks, etc.).

Second Embodiment—Inflatable Bladders with Localized Interfering Pockets

Figure 6A:
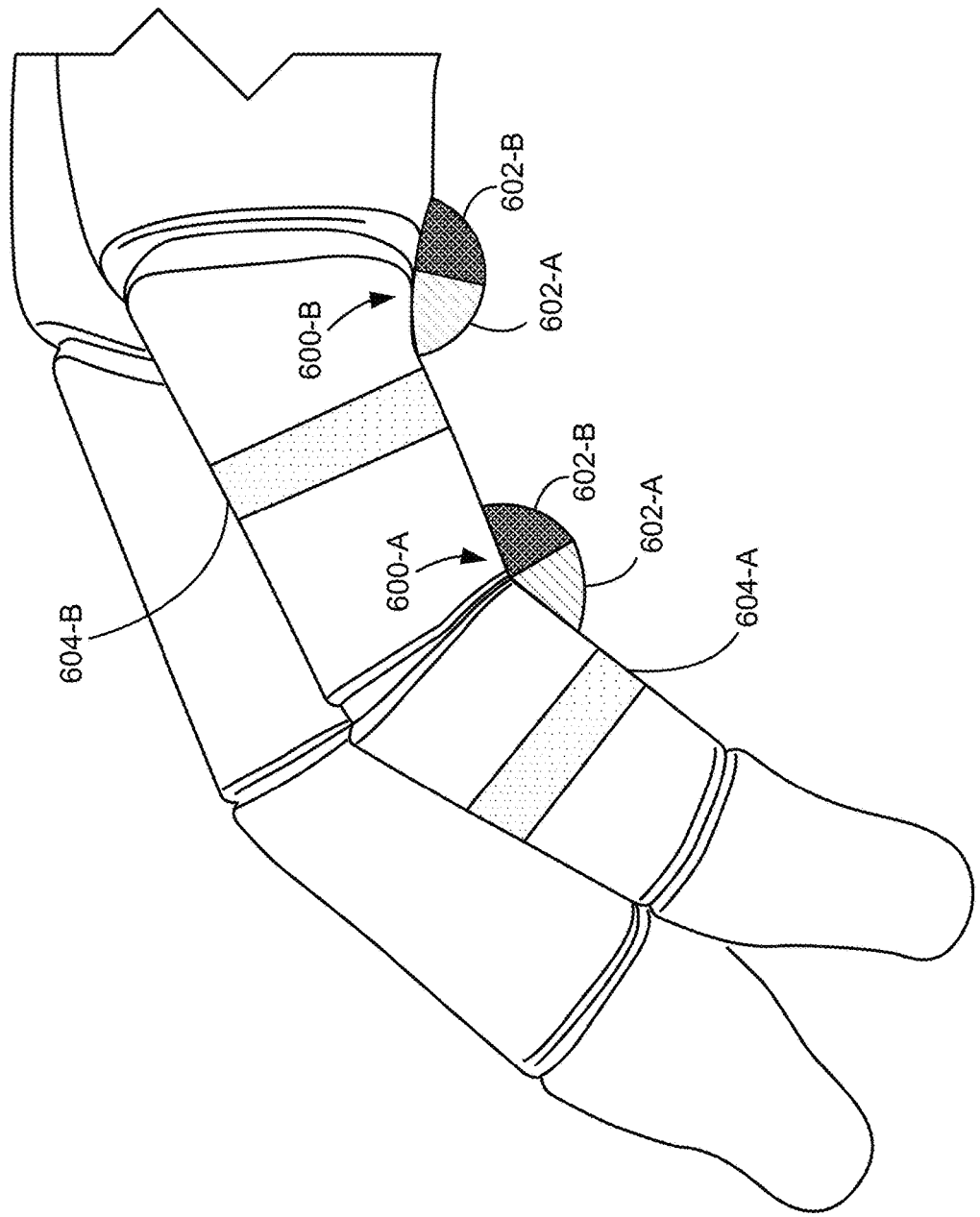
FIG. 6A shows an example haptic-feedback assembly on a portion of a user's body in accordance with some embodiments.

FIGS. 6A-6D are directed toward embodiments that include inflatable bladders with localized interfering pockets (as opposed to distributed interfering pockets). FIG. 6A shows an example haptic-feedback assembly 122 on a portion of a user's body in accordance with some embodiments. The haptic-feedback assembly 122 of FIG. 6A includes a first inflatable bladder 600-A and a second inflatable bladder 600-B that are secured to a user's finger by a first grounding component 604-A and a second grounding component 604-B. In some embodiments, the first and second grounding components 604 are physical straps that are tightened around the user's finger. In some other embodiments, the first and second grounding components 604 themselves include inflatable bladders that are inflated to secure the first inflatable bladder 600-A and the second inflatable bladder 600-B to the user's finger. While not shown, one or more additional grounding components 604 may be included in the haptic-feedback assembly 122 of FIG. 6A to secure the inflatable bladders 600 to the user's finger.

The first inflatable bladder 600-A and the second inflatable bladder 600-B are both examples of the inflatable bladder 204. As shown, the first inflatable bladder 600-A, which is positioned at the proximal interphalangeal joint, includes a first pocket 602-A and a second pocket 602-B. Likewise, the second inflatable bladder 600-B, which is positioned at the metacarpophalangeal joint, includes a first pocket 602-A and a second pocket 602-B. The first pocket 602-A and the second pocket 602-B in the inflatable bladders 600 of FIG. 6A are configured to operate in the manner explained above with reference to FIGS. 5A-5D. For example, in FIG. 6A, the first inflatable bladder 600-A and the second inflatable bladder 600-B are both in a pressurized state, and, consequently, the first pocket 602-A and the second pocket 602-B in each inflatable bladder 600 are configured to impart one or more directional forces onto the user at respective target locations that impede movement of the user's finger (i.e., resist finger flexion). As explained above, the one or more directional forces imparted on the user by the first pocket 602-A and the second pocket 602-B are caused by the pockets interfering with each other when inflated (e.g., the user attempts to curl his or her finger, which causes the inflated pockets to press against each other, thereby preventing the user from curl his or her finger past a certain point).

In some embodiments, the first inflatable bladder 600-A and the second inflatable bladder 600-B are fluidically coupled to the source 210 by the same conduit 208. In such embodiments, the first inflatable bladder 600-A and the second inflatable bladder 600-B are pressurized to approximately the same pressure at the same time when in the pressurized state. In some other embodiments, the first inflatable bladder 600-A is fluidically coupled to the source 210 by a first conduit 208 and the second inflatable bladder 600-B is fluidically coupled to the source 210 by a second conduit 208. In such embodiments, the first inflatable bladder 600-A and the second inflatable bladder 600-B can be inflated to different pressures at different times (or the same pressure at the same time).

Figure 6B:
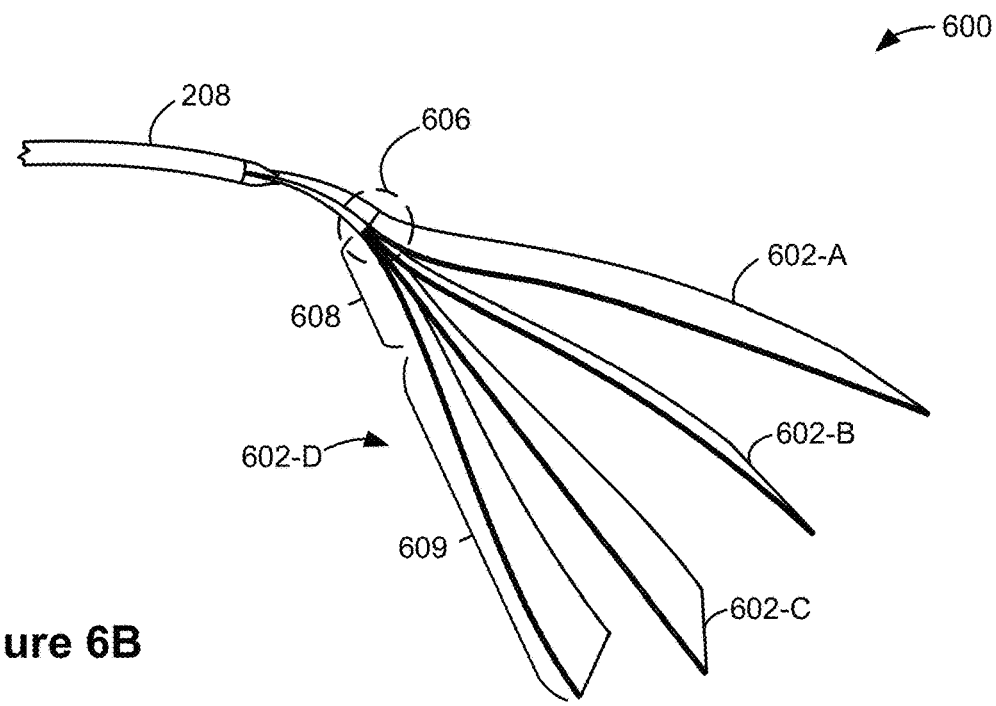
FIGS. 6B and 6C show a representative inflatable bladder in different states in accordance with some embodiments.
Figure 6C:
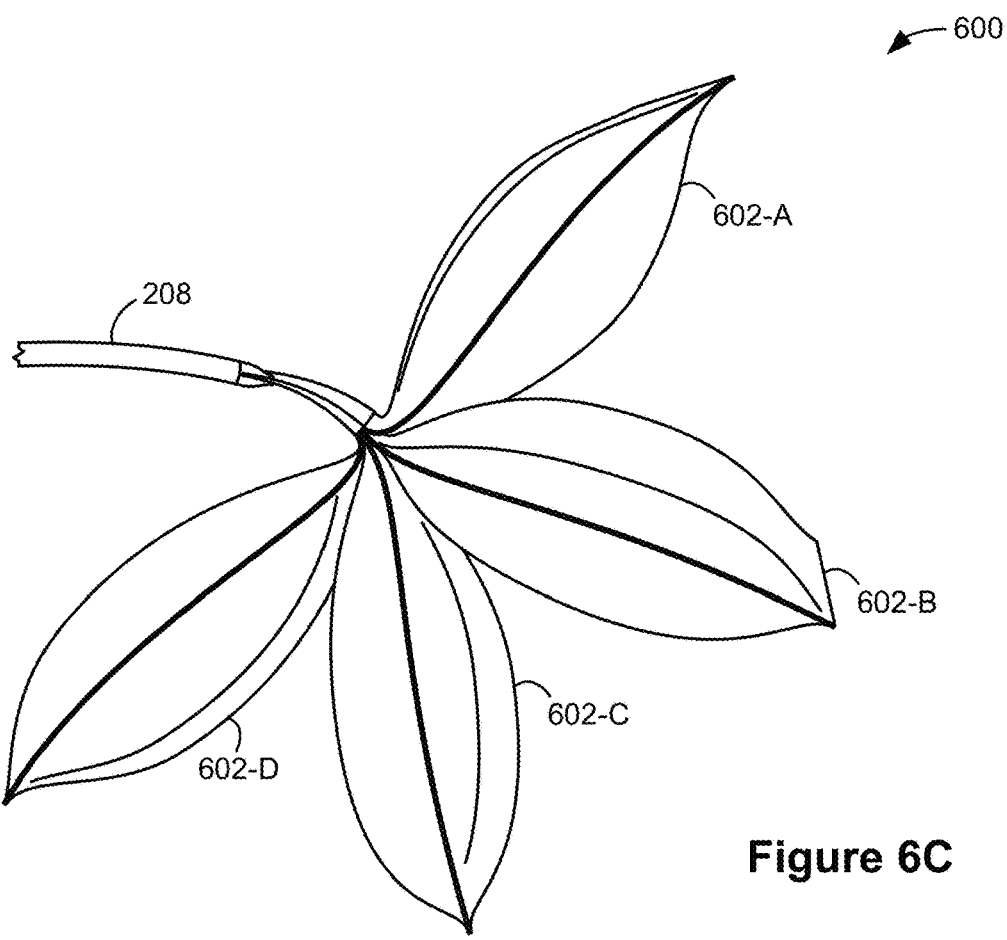

FIGS. 6B and 6C show a representative inflatable bladder 600 in different states in accordance with some embodiments. In particular, FIG. 6B shows the representative inflatable bladder 600 in an unpressurized state while FIG. 6C shows the representative inflatable bladder 600 in a pressurized state. In some instances, the representative inflatable bladder 600 is referred to as an "origami actuator" because the actuator collapses into a thin multi-layer structure in the unpressurized/deflated state. However, when inflated, the actuator expands in a rotary manner and the inflated pockets 602 interfere to resist finger flexion (as explained above with reference to FIGS. 5A-5D). Furthermore, the collapsible origami structure of the representative inflatable bladder 600 ensures that torque increases gradually and in a continuous manner, which results in a perceptually believable haptic stimulation. As shown with reference to FIG. 6A, this design has localized bladders 600 can be positioned at finger joints, and each of which has a small volume, meaning that the bladders 600 can be inflated and deflated in a short duration (i.e., they have fast response times).

The representative inflatable bladder 600 includes a plurality of pockets 602-A-602-D. As shown with reference to the pocket 602-D, each pocket 602 includes an end portion 608 and a body portion 609. Furthermore, end portions 608 of the plurality of pockets 602-A-602-D are coupled with each other at a connection point 606. Notably, the body portions of the plurality of pockets 602-A-602-D are decoupled from each other, which reduces encumbrances imposed on the user by the representative inflatable bladder 600 when the inflatable bladder 600 is in the unpressurized state. Furthermore, the decoupled design of the plurality of pockets 602-A-602-D allows for the pockets 600 to independently collapse onto each other. Put another way, when the plurality of pockets 602-A-602-D are not inflated, the plurality of pockets 602-A-602-D are configured to collapse such that the respective body portions 609 lay adjacent to each other.

As shown with reference to FIG. 6C, the plurality of pockets 602-A-602-D are configured to, when inflated, expand such that the respective body portions 609 of the plurality of pockets 602-A-602-D fan out away from the connection point 606. Because the representative inflatable bladder 600 includes four pockets 602, three distinct interference regions 505 are created when the representative inflatable bladder 600 is in the pressurized state. This particular design ensures that torque increases gradually and in a continuous manner, as mentioned above. For example, as the plurality of pockets 602-A-602-D inflate, a degree of contact between neighboring pockets 602 gradually increases.

Figure 6D:
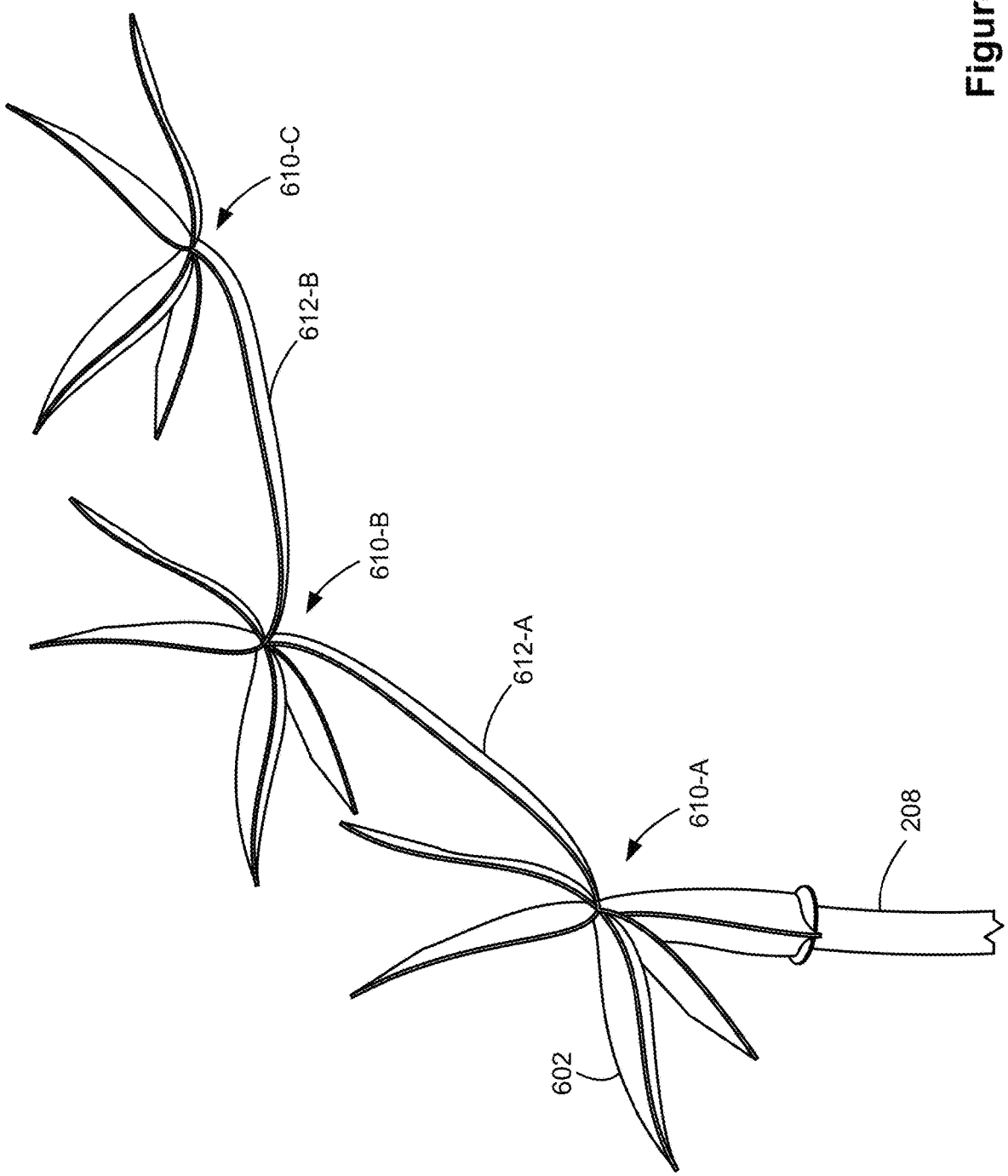
FIG. 6D shows another representative inflatable bladder in accordance with some embodiments.

FIG. 6D shows an alternate embodiment of the representative inflatable bladder 600 in accordance with some embodiments. In this particular example, the representative inflatable bladder 600 includes multiple pocket clusters 610-A, 610-B, and 610-C, whereby each pocket cluster 610 is designed to be positioned at a finger joint. Furthermore, the multiple pocket clusters 610-A, 610-B, and 610-C are interconnect via passages 612-A, 612-B, which allows for each cluster 610 to be fluidically coupled to the source 210. As also shown, each pocket cluster 610 includes four pockets 602. However, in some embodiments, each pocket cluster 610 includes fewer than or more than four pockets 602. Additionally, the multiple pocket clusters 610-A, 610-B, and 610-C may have the same number of pockets 602 or different number of pockets 602. For example, because greater forces are needed to impede movement of different finger joints, a number of pockets 602 in a given cluster 610 may be tailored according to a force requirement for a particular finger joint. To illustrate, greater forces are needed to resist finger flexion at the proximal interphalangeal joint compared to the distal interphalangeal joint. As such, the cluster 610-B may have more pockets 602 than the cluster 610-C.

Third Embodiment—Inflatable Bladders with Distributed Interfering Pockets

Figure 7A:
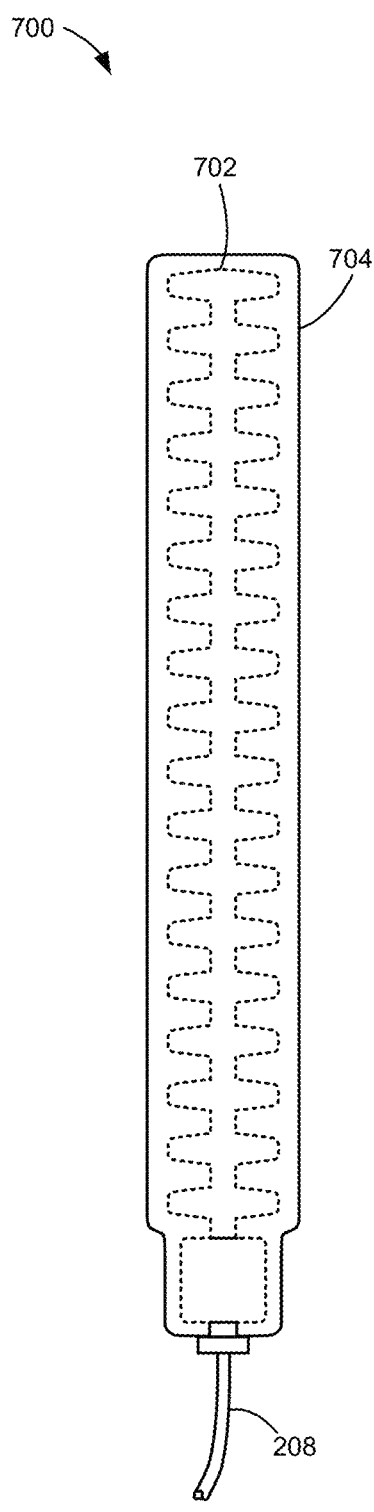
FIGS. 7A and 7B show top and bottom views, respectively, of a representative inflatable bladder in accordance with some embodiments.
Figure 7B:
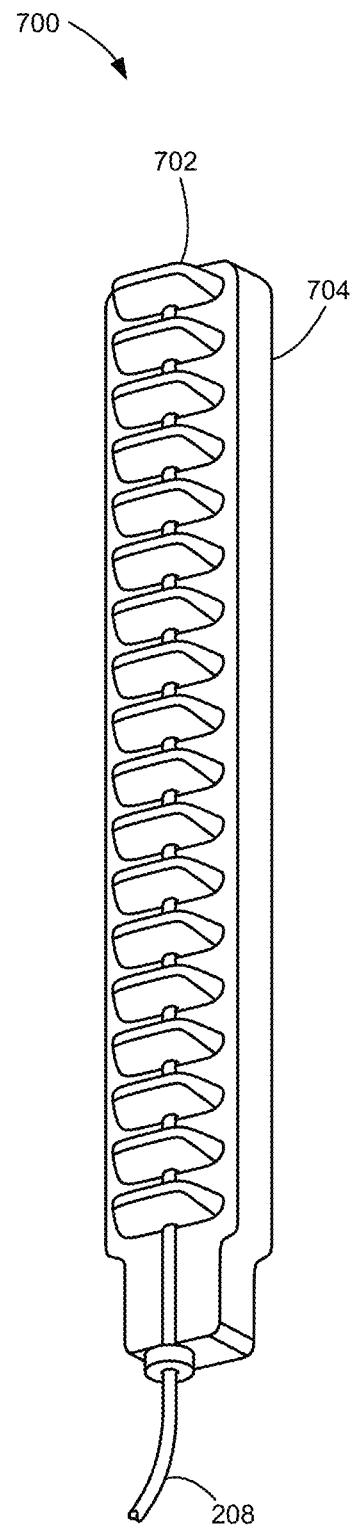
Figure 7C:
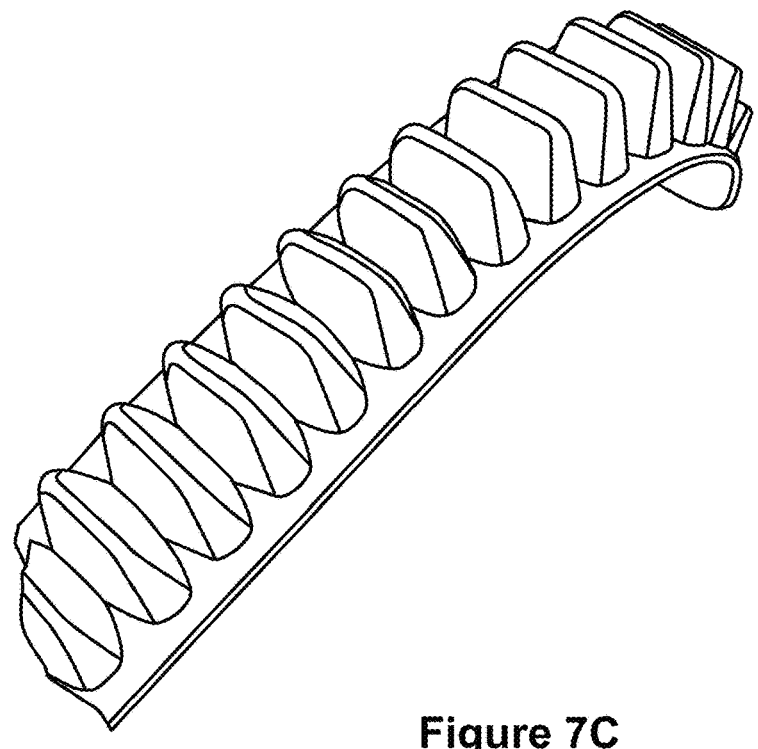
FIGS. 7C and 7D show the representative inflatable bladder of FIGS. 7A and 7B in different pressurized states in accordance with some embodiments.
Figure 7D:
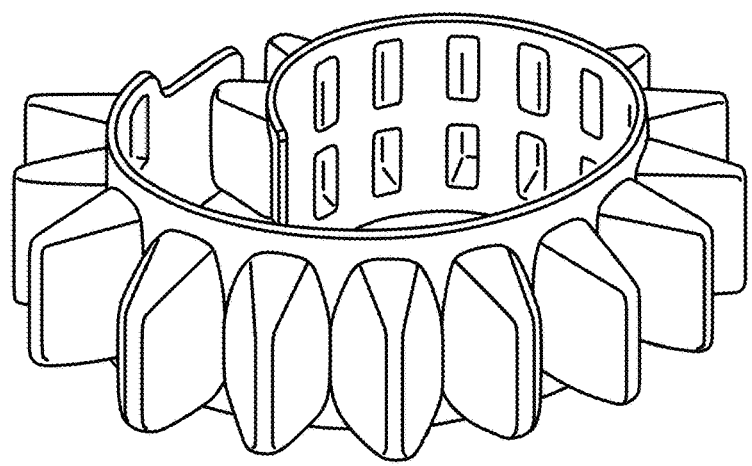
Figure 7E:
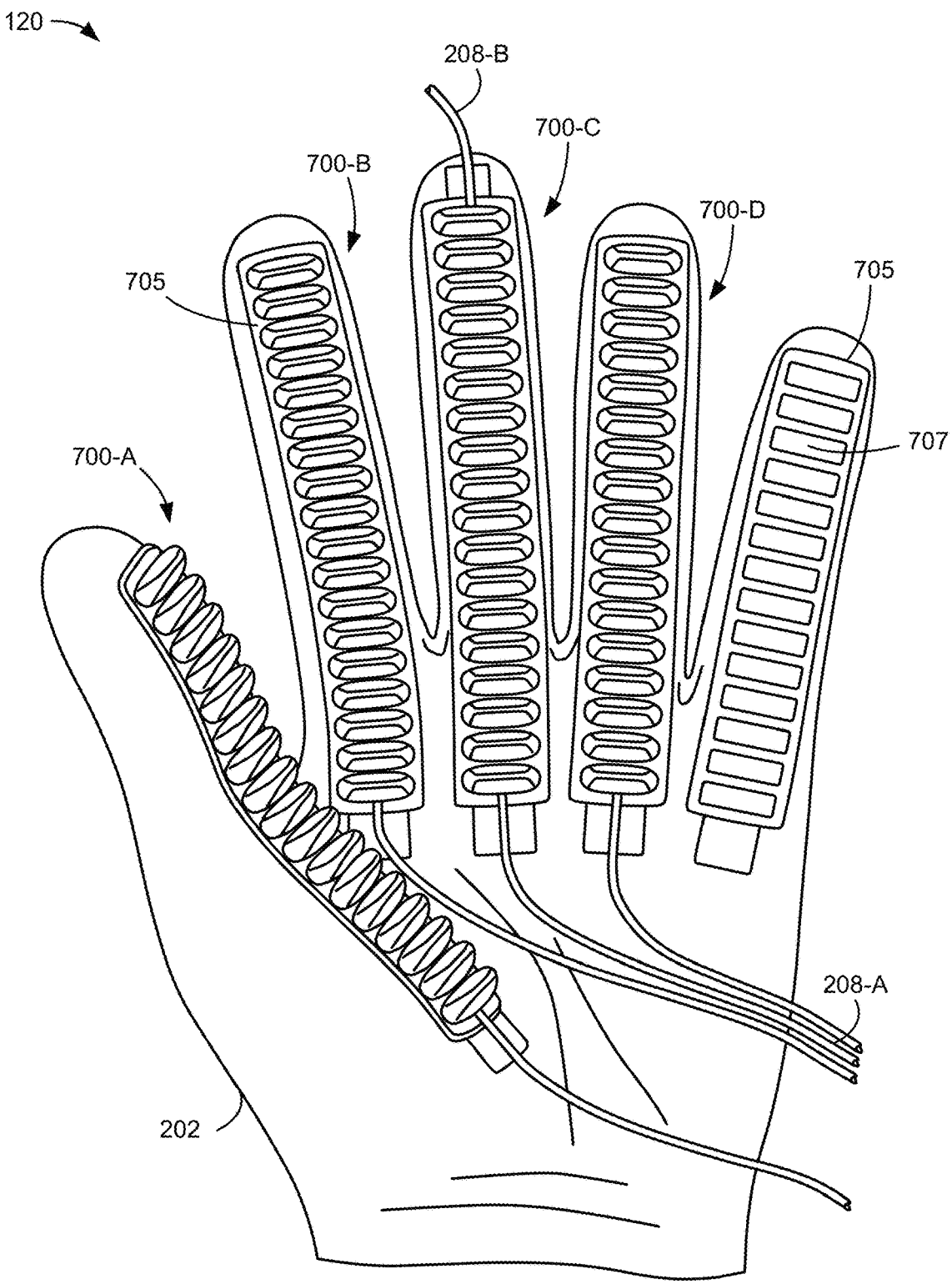
FIG. 7E shows an example wearable device that includes multiple instances of the inflatable bladder of FIGS. 7A and 7B in accordance with some embodiments.

FIGS. 7A-7E are directed toward embodiments that include inflatable bladders 700 with distributed interfering pockets. The inflatable bladders 700 discussed with reference to FIGS. 7A-7E are examples of the inflatable bladder 204. At a high level, the inflatable bladders 700 include a series of pockets 702 designed to be distributed along a portion of the user's body, such as entire fingers as shown in FIG. 7E. The pockets 702 are thin-walled and made from an elastic material, such as thermoplastic polyurethane (TPU), meaning that the pockets 702 can be easily bent when unpressurized, and, therefore, the inflatable bladders 700 have low encumbrance when unpressurized. As the bladder 700 is inflated, the pockets 702 expand, become semi-rigid, and interfere with each other to resist finger flexion. The distributed design of the inflatable bladders 700 allows for the inflatable bladders 700 to fit a wide range of users.

FIGS. 7A and 7B show top and bottom views of a representative inflatable bladder 700. As shown, the representative inflatable bladder 700 includes (i) an elongated substrate 704 forming a first side of the representative inflatable bladder 700 and (ii) two or more pockets 702 (a) that are distributed along a length of the elongated substrate 704 and (b) form a second side of the representative inflatable bladder 700. In some embodiments, the two or more pockets 702 are integrally formed with the elongated substrate 704, while in other embodiments the two or more pockets 702 are adhered with (or otherwise coupled to) the elongated substrate 704. In FIGS. 7A-7B, the representative inflatable bladder 700 is in an unpressurized state, such that none of the two or more pockets 702 are touching each other (i.e., interfering with one another).

The elongated substrate 704 may be made from an inelastic textile or polymer, while the two or more pockets 702 are made from an elastic material, as discussed above. A portion of the elongated substrate 704 that contacts the user's body (i.e., the portion shown in FIG. 7A) is designed to remain flat. In this way, the representative inflatable bladder 700 rests somewhat unnoticed on the user wearing the wearable device 120.

In some embodiments, the two or more pockets 702 have the same size and shape. In some other embodiments, one or more pockets of the two or more pockets 702 have different sizes and shapes. For example, pockets 702 positioned toward the conduit 208 may have elongated shapes while pockets 702 positioned toward a fingertip may have shortened shapes (or vice versa). Varying a shape/profile of the two or more pockets 702 can be used to control an amount of resistance created by the inflatable bladder 700 (especially the amount of resistance created at specific target areas, such as finger joints).

FIGS. 7C and 7D show the representative inflatable bladder 700 in different pressurized states in accordance with some embodiments. In particular, FIG. 7C shows the representative inflatable bladder 700 in a low pressure state (e.g., the representative inflatable bladder 700 is pressurized to some minimal degree above ambient pressure). In the low pressure state, the representative inflatable bladder 700 is partially curved as a result of the two or more pockets 702 partially touching (i.e., pressing against) each other. More specifically, respective base portions of neighboring pockets 702 press against each other, which causes, in essence, a length of the second side of the inflatable bladder 700 to increase relative to a length of the first side of the inflatable bladder 700. The newly introduced difference in length causes the inflatable bladder 700 to curve in the manner shown in FIG. 7C. In the state shown in FIG. 7C, the representative inflatable bladder 700 would impart minimal forces to a user, such that finger flexion would be impeded, but only slightly.

FIG. 7D shows the representative inflatable bladder 700 in a high pressure state (e.g., the representative inflatable bladder 700 is pressurized to some threshold pressure). In the high pressure state, the representative inflatable bladder 700 is curved substantially as a result of the two or more pockets 702 pushing against each other. More specifically, neighboring pockets 702 are pressed against each other due to the representative inflatable bladder 700 being inflated at the high pressure, which causes a length of the second side of the inflatable bladder 700 to increase substantially relative to a length of the first side of the inflatable bladder 700. The newly introduced difference in length (which is greater than the difference in length introduced in FIG. 7C) causes the inflatable bladder 700 to curve in the manner shown in FIG. 7D. In the state shown in FIG. 7D, the representative inflatable bladder 700 would impart significant forces to a user, such that finger flexion would be greatly impeded (e.g., a user would struggle to bend his or her finger).

In some embodiments, the two or more pockets 702 have a predefined shape when inflated to a predefined pressure, and the predefined shape is dependent, at least in part, on a wall thickness of each pocket of the two or more pockets 702. In some embodiments, one or more pockets have a wall thickness ranging from 2-6 millimeters (preferably 4 millimeters).

FIG. 7E shows an example wearable device 120 that includes multiple inflatable bladders 700 in accordance with some embodiments. As shown, inflatable bladders 700 are coupled to a wearable structure 202 (e.g., glove) so that their respective pockets 702 are positioned facing away from a palmer side of the user's hand. This is also true for the inflatable bladders 600 (i.e., the inflatable bladders 600 are coupled to a wearable structure 202 (e.g., glove) so that their respective pockets 602 face away from a palmer side of the user's hand). In contrast, the inflatable bladders 300 are coupled to the wearable structure 202 so that their barbs 302 face from a palmer side of the user's hand.

In some embodiments, one or more of the inflatable bladders 700 are fluidically coupled to the source 210 by a single conduit 208, as shown with inflatable bladders 700-A, 700-B, and 700-D. Alternatively or in addition, in some embodiments, one or more of the inflatable bladders 700 are fluidically coupled to the source 210 by multiple conduits 208-A, 208-B. Attaching multiple conduits to a single inflatable bladder 700 allows the source 210 to add and remove fluid to the bladder 700 at a faster rate.

In some embodiments, the wearable structure 202 includes a grounding structure 705 that includes a plurality of openings 707 sized to receive the pockets 702 of the inflatable bladders 700. For ease of illustration, the inflatable bladder 700 on the user's pinky finger has been removed to show a structure of the grounding structure 705. The grounding structure 705 is configured to fix the pockets 702 of the inflatable bladders 700 in a particular orientation, so that the pockets 702 do not shift or otherwise rotate from their desired positions. The grounding structure 705 may be made from an inextensible material, which helps fix the pockets 702 at their desired positions.

Fourth Embodiment—Inflatable Bladders with Integrated Channels

Figure 8A:
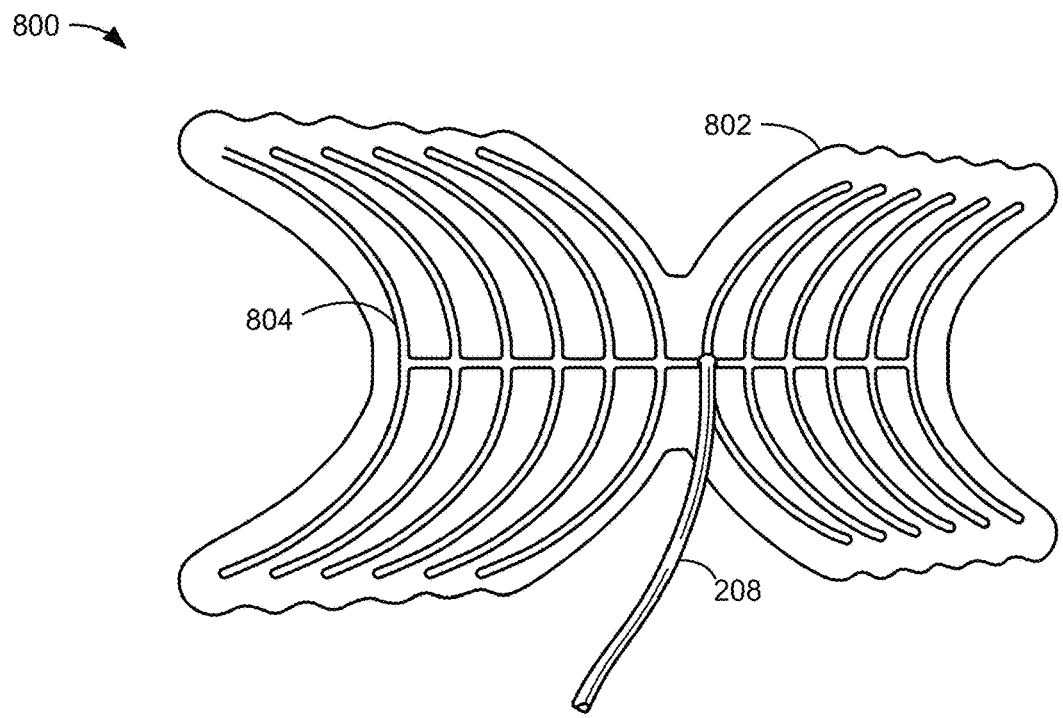
FIGS. 8A-8C show another representative inflatable bladder in different pressurized states in accordance with some embodiments.
Figure 8B:
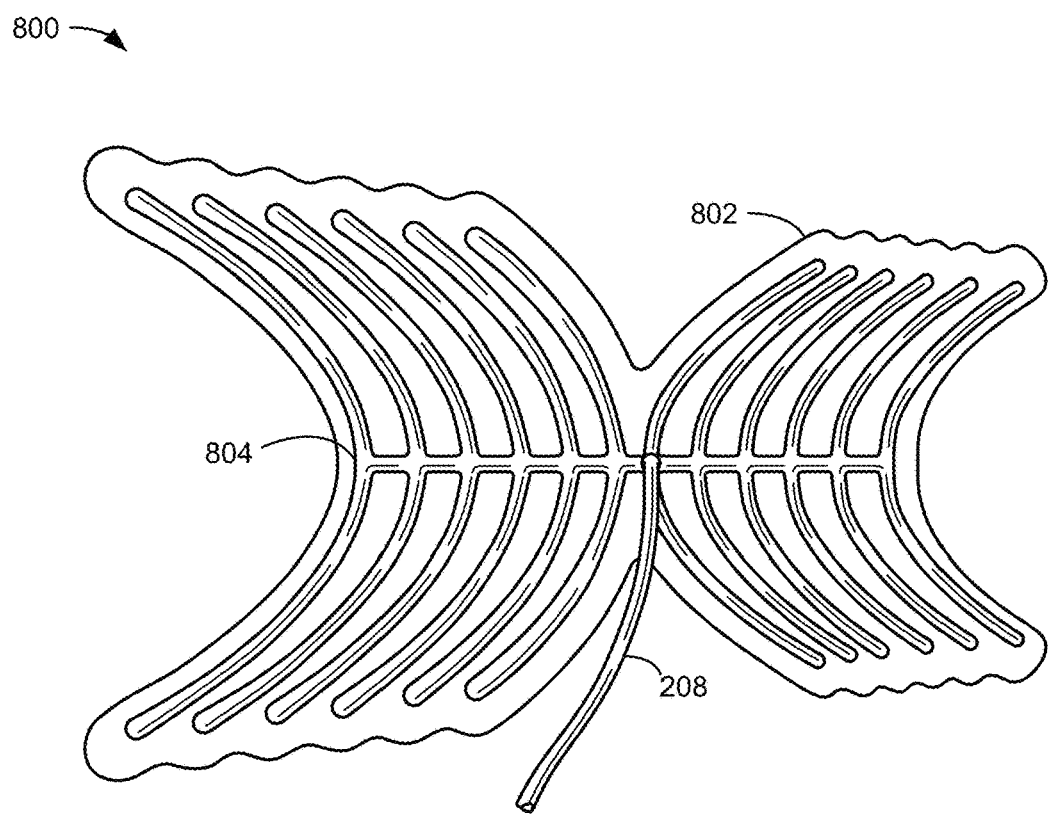
Figure 8C:
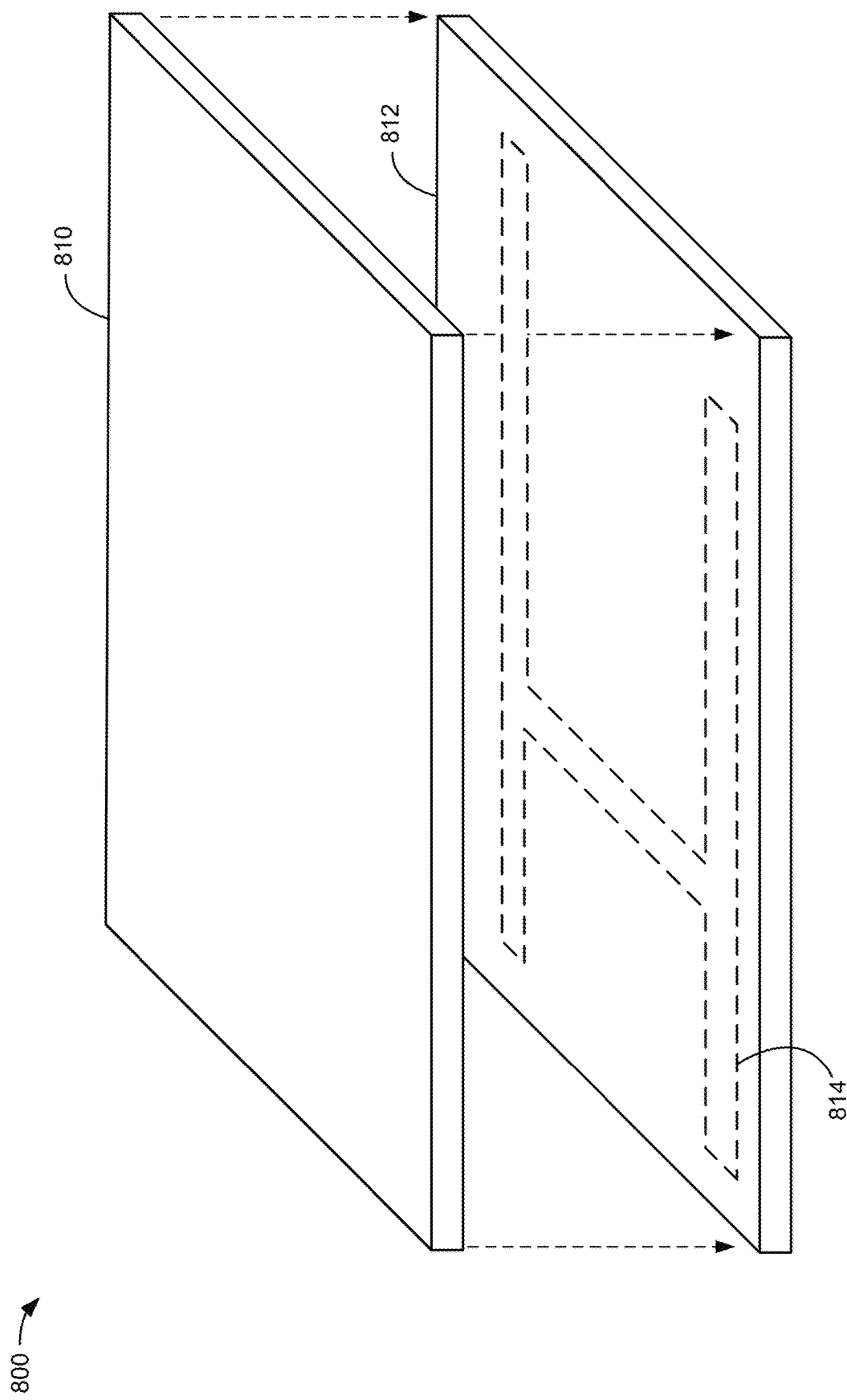

FIGS. 8A-8C are directed toward embodiments that include an inflatable bladder 800 with integrated channels 804 (e.g., fluid channels). In particular, FIG. 8A shows the inflatable bladder 800 in an unpressurized state while FIG. 8B shows the inflatable bladder 800 in a pressurized state. FIG. 8C shows components of the inflatable bladder 800, including a first substrate 810 that is bonded to a second substrate 812, as shown in FIG. 8C. Notably, the inflatable bladder 800 also includes an unbonded region 814 between the first substrate 810 and the second substrate 812. The unbonded region 814 forms the integrated channels 804 shown in FIGS. 8A and 8B. Note that the unbonded region 814 has a simplified shape in FIG. 8C for ease of illustration.

In some embodiments, the integrated channels 804 are created during a compression operation where the first substrate 810 is compressed against the second substrate 812, and heat is also applied. To prevent the first substrate 810 from bonding with the second substrate 812 in the unbonded region 814, a jig having a shape of the unbonded region 814 is used to insulate the first substrate 810 and/or the second substrate 812 from heat during the compression operation. For example, the first and second substrates 810, 812 may be polymer substrates that bond together under heat and pressure. Accordingly, the jig is used to insulate a portion of the first and second substrates 810, 812 from heat, thereby ensuring that the substrates do not bond together at the unbonded region 814.

In use, the integrated channels 804 of the inflatable bladder 800 are configured to expand in response to receiving fluid from the source 210 (e.g., via the conduit 208). The inflatable bladder 800 is designed to deformed in one or more directions in response to the integrated channels 804 expanding. It is this deformation of the inflatable bladder 800 that imparts a haptic stimulation onto a user. In some instance, a user may also experience a pinching stimulation in areas between neighboring channels of the integrated channels 804. While not shown in FIGS. 8A-8C, the inflatable bladder 800 is also designed to be coupled with a wearable structure 202. Accordingly, when the inflatable bladder 800 deforms, a person wearing the wearable structure 202 feels the haptic stimulation, which in some cases, is a pinching stimulation, while in other situations, is a little gripping stimulation.

Due to the seamless design of the inflatable bladder 800 and the fact that the inflatable bladder 800 can be made from highly elastic materials (e.g., silicone), the inflatable bladder 800 is able to easily contour to the user's body. This is particularly useful on areas of the body with complex geometries, such as the palmar surface of the human thumb.

Methods of Operation

Figure 9:
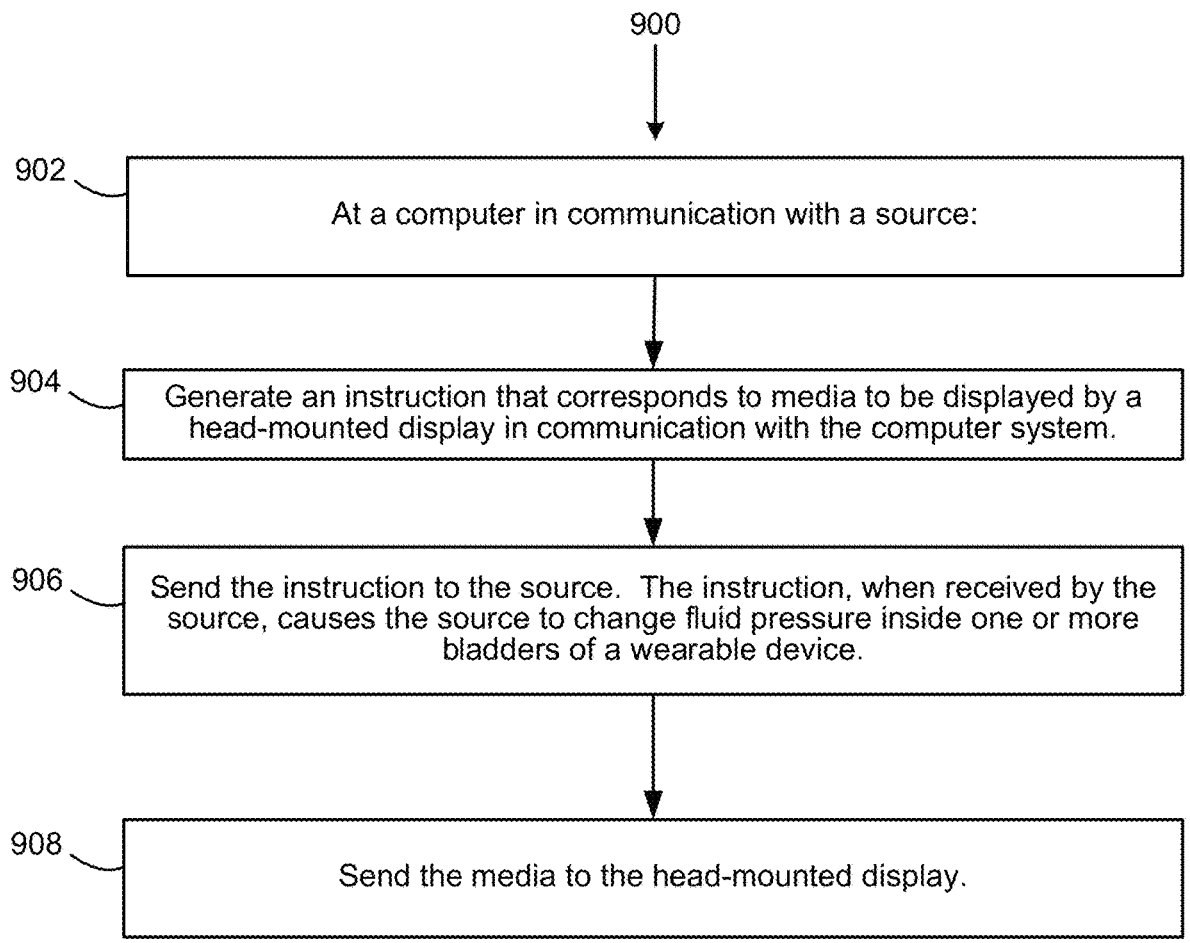
FIG. 9 is a flow diagram illustrating a method of creating haptic stimulations in accordance with some embodiments.

FIG. 9 is a flow diagram illustrating a method 900 of creating haptic stimulations in accordance with some embodiments. The steps of the method 900 may be performed (902) by a computer 130. FIG. 9 corresponds to instructions stored in a computer memory or computer readable storage medium (e.g., the memory of the computer system 130). For example, the operations of the method 900 are performed, at least in part, by a communication interface 136 and an artificial-reality generation module (e.g., part of the engine 134). It is noted that the method described below can be implemented with any of the wearable devices and haptic-feedback mechanisms discussed above.

The method 900 includes generating (904) an instruction that corresponds to media (e.g., visual data) to be displayed by a head-mounted display 110 in communication the computer system (and/or corresponds to information received from one or more sensors 124 of the wearable device 120 and/or information received from one or more sensors 114 of the head-mounted display 110). In some embodiments, the computer system generates the instruction based on information received from the sensors on the wearable device. Alternatively or in addition, in some embodiments, the computer system generates the instruction based on information received from the sensors on the head-mounted display. For example, cameras (or other sensors 114) on the head-mounted display may capture movements of the wearable device, and the computer system can use this information when generating the instruction.

The method 900 further includes sending (906) the instruction to a fluid source 210 in communication with the computer system (e.g., send the instruction in a communication signal from a communication interface). The instruction, when received by the source, causes the source to change a pressure inside one or more bladders 204 of the wearable device 120. In doing so, a wearer of the wearable device experiences a haptic stimulation that corresponds to the data. In some embodiments, the instruction specifies the change in the pressure to be made by the source. In some situations, instead of the computer system sending the instruction to the source, the computer system sends the instruction to the wearable device, and in response to receiving the instruction, the wearable device sends the instruction to the source. The source is discussed in further detail above with reference to FIG. 2.

After (or while, or before) sending the instruction, the method 900 also includes sending (908) the media to the head-mounted display. For example, the head-mounted display may receive visual data from the computer system, and may in turn display the visual data on its display(s). As an example, if the computer system receives information from the sensors 124 of the wearable device 120 that the user has closed his fingers around a position corresponding to a coffee mug in the virtual environment and raised his hand, a simulated hand in a virtual-reality application picks up the virtual coffee mug and lifts it to a corresponding height. Generating and sending media is discussed in further detail above with reference to FIG. 1.

In conjunction with displaying the visual data (or other media), one or more bladders of the wearable device are inflated (or deflated) to the desired pressure (as noted above). As an example, the wearable device may include: (i) a wearable structure to be worn on a portion of a user's body, and at least one inflatable bladder, coupled to the wearable structure, that includes two or more pockets positioned at a target location on the wearable structure. In such embodiments, the two or more pockets are configured to, when inflated, impart one or more directional forces onto the user at the target location that impede movement of the portion of the user's body. Furthermore, the one or more directional forces are caused by the two or more pockets interfering with each other, when inflated.

In some embodiments, the one or more directional forces imparted onto the user at the target location simulate (i.e., mimic) forces induced by physical objects at the target location (e.g., finger joint) during natural-object interaction. Using the coffee mug example from above, if the computer system receives information that the user has closed his fingers around a position corresponding to a coffee mug in the virtual environment, then the one or more directional forces imparted onto the user at the target location simulate forces induced by a physical coffee mug at a finger joint during natural hand-object interaction. Moreover, a magnitude of the one or more directional forces imparted onto the user at the target location may be selected based on the physical object. For example, the one or more directional forces may have a greater magnitude when the object is solid and/or heavy relative to a magnitude of the one or more directional forces when the object is soft and/or light.

In another example, the wearable device may include: (i) a wearable structure to be worn on a portion of a user's body, and (ii) an inflatable bladder, coupled to the wearable structure at a target location, that includes opposing first and second surfaces, whereby the inflatable bladder is configured to receive a fluid from a source. In such embodiments, the first surface of the inflatable bladder includes a plurality of barbs positioned to interact with the user's body at the target location, whereby the plurality of barbs are configured to protrude from the first surface in response to the inflatable bladder receiving the fluid from the source (i.e., in response to the inflatable bladder being inflated by the source).

In some embodiments, the computer and the head-mounted display together form an artificial-reality system. Furthermore, in some embodiments, the artificial-reality system is a virtual-reality system 1200. Alternatively, in some embodiments, the artificial-reality system is an augmented-reality system 1100 or some other artificial-reality system 1000. In some embodiments, the data presented to the user by the artificial-reality system includes visual media displayed on one or more displays of the virtual-reality or augmented-reality system.

Embodiments of this disclosure may include or be implemented in conjunction with various types of artificial-reality systems. Artificial reality may constitute a form of reality that has been altered by virtual objects for presentation to a user. Such artificial reality may include and/or represent virtual reality (VR), augmented reality (AR), mixed reality (MR), hybrid reality, or some combination and/or variation of one or more of the these. Artificial-reality content may include completely generated content or generated content combined with captured (e.g., real-world) content. The artificial-reality content may include video, audio, haptic feedback, or some combination thereof, any of which may be presented in a single channel or in multiple channels (such as stereo video that produces a three-dimensional effect to a viewer). Additionally, in some embodiments, artificial reality may also be associated with applications, products, accessories, services, or some combination thereof, which are used, for example, to create content in an artificial reality and/or are otherwise used in (e.g., to perform activities in) an artificial reality.

Artificial-reality systems may be implemented in a variety of different form factors and configurations. Some artificial-reality systems are designed to work without near-eye displays (NEDs), an example of which is the artificial-reality system 1000 in FIG. 10. Other artificial-reality systems include an NED, which provides visibility into the real world (e.g., the augmented-reality (AR) system 1100 in FIG. 11) or that visually immerses a user in an artificial reality (e.g., the virtual-reality (VR) system 1200 in FIG. 12). While some artificial-reality devices are self-contained systems, other artificial-reality devices communicate and/or coordinate with external devices to provide an artificial-reality experience to a user. Examples of such external devices include handheld controllers, mobile devices, desktop computers, devices worn by a user (e.g., wearable device 120), devices worn by one or more other users, and/or any other suitable external system.

Figure 10:
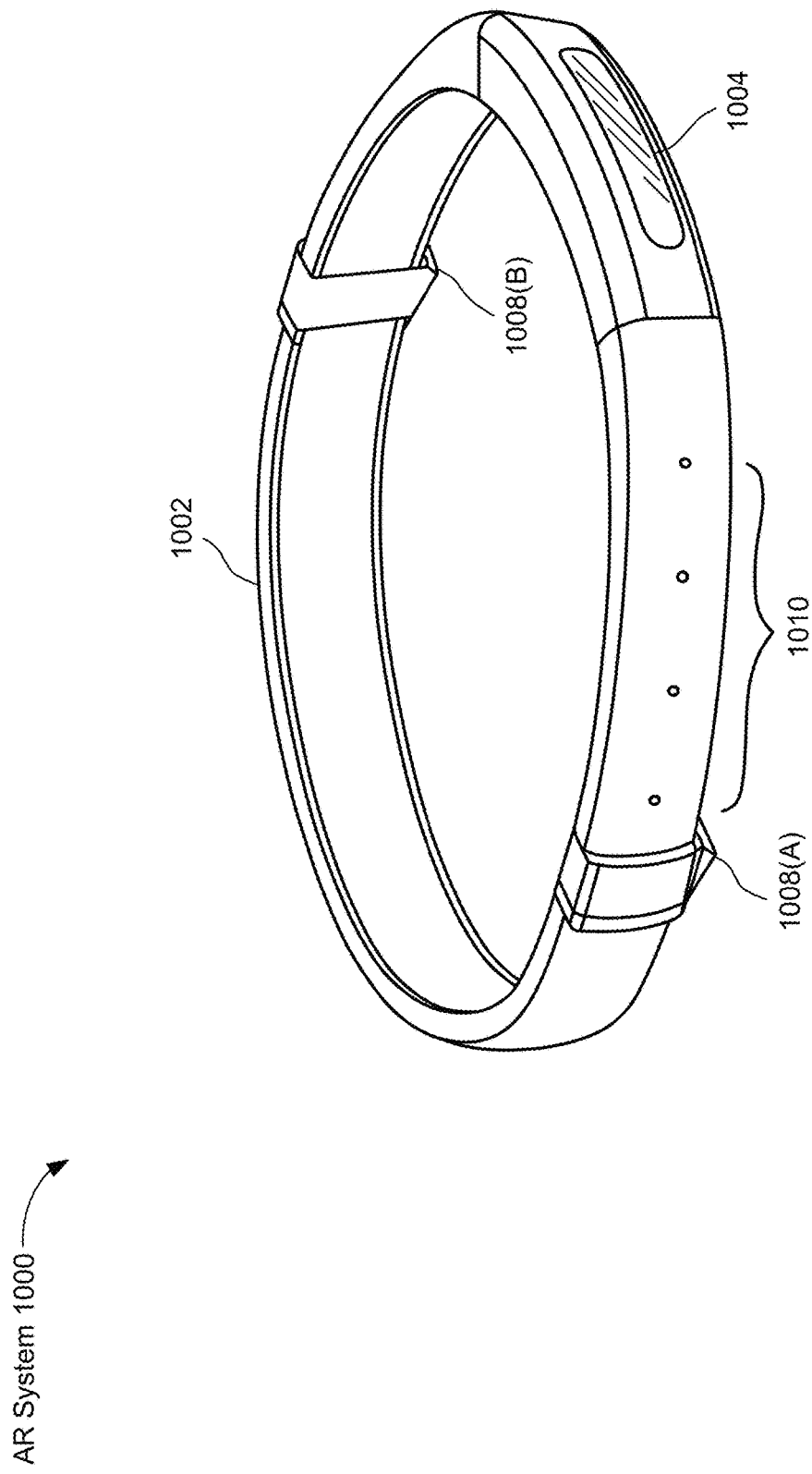
FIG. 10 illustrates an embodiment of an artificial-reality device.
Figure 11:
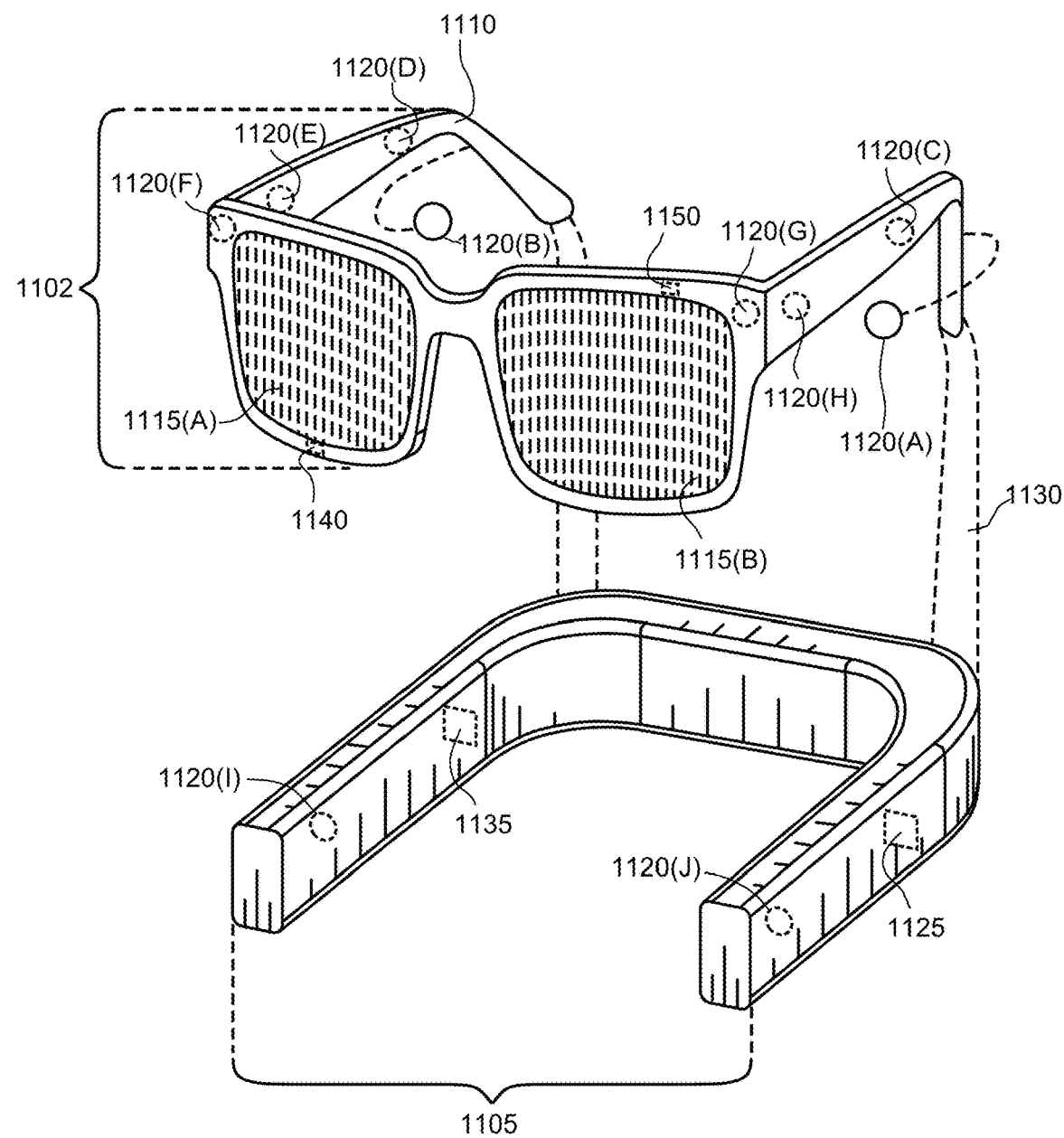
FIG. 11 illustrates an embodiment of an augmented-reality headset and a corresponding neckband.
Figure 12:
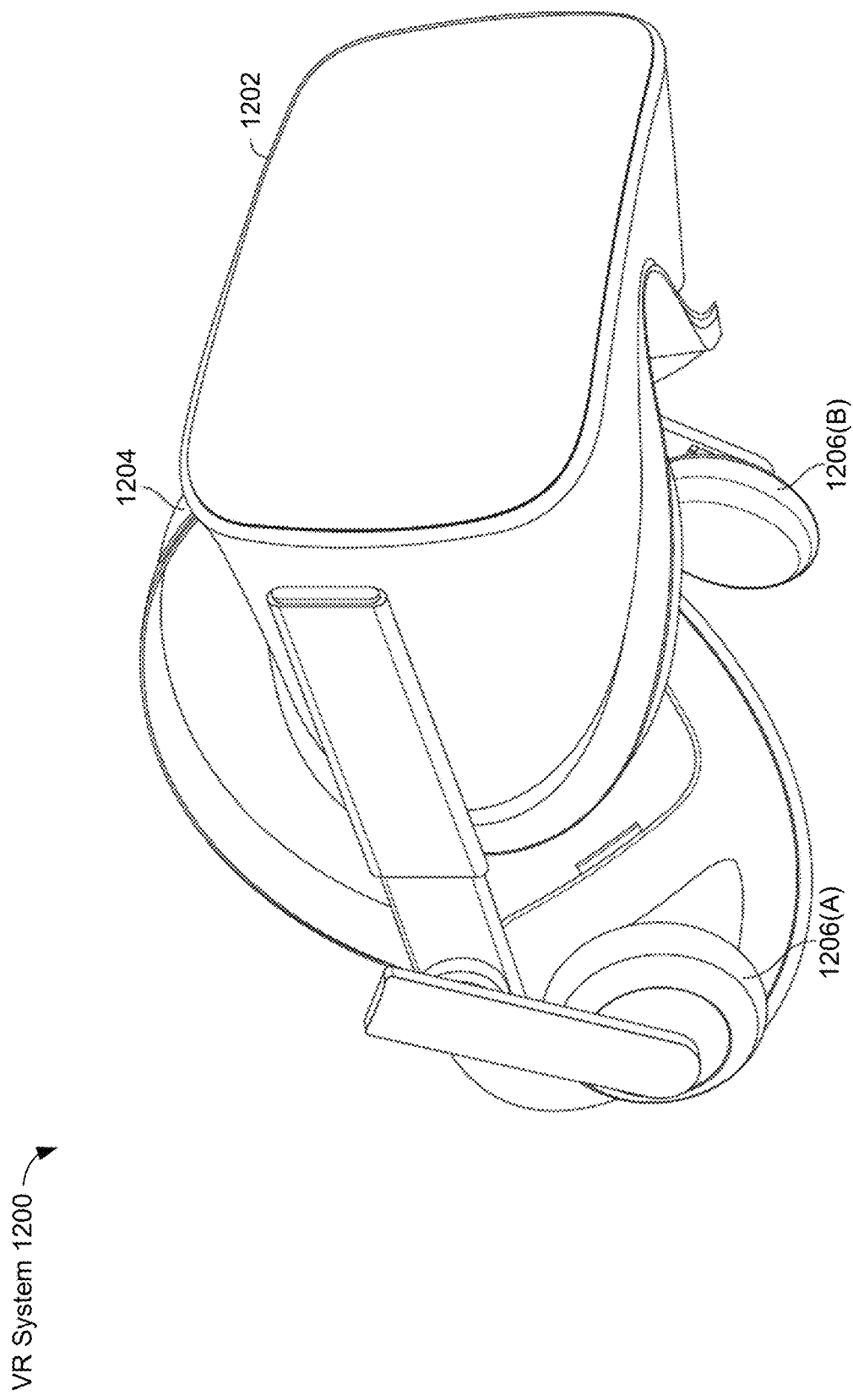
FIG. 12 illustrates an embodiment of a virtual-reality headset.

FIGS. 10-12 provide additional examples of the devices used in a system 100. The artificial-reality system 1000 in FIG. 10 generally represents a wearable device dimensioned to fit about a body part of a user. The artificial-reality system 1000 may include the functionality of a wearable device, and may include functions not described above. As shown, the artificial-reality system 1000 includes a frame 1002 (e.g., a band or wearable structure) and a camera assembly 1004, which is coupled to the frame 1002 and configured to gather information about a local environment by observing the local environment (and may include a display 1004 that displays a user interface). In some embodiments, the artificial-reality system 1000 includes output transducers 1008(A) and 1008(B) and input transducers 1010. The output transducers 1008(A) and 1008(B) may provide audio feedback, haptic feedback, and/or content to a user, and the input audio transducers may capture audio (or other signals/waves) in a user's environment.

Thus, the artificial-reality system 1000 does not include a near-eye display (NED) positioned in front of a user's eyes. Artificial-reality systems without NEDs may take a variety of forms, such as head bands, hats, hair bands, belts, watches, wrist bands, ankle bands, rings, neckbands, necklaces, chest bands, eyewear frames, and/or any other suitable type or form of apparatus. While the artificial-reality system 1000 may not include an NED, the artificial-reality system 1000 may include other types of screens or visual feedback devices (e.g., a display screen integrated into a side of the frame 1002).

The embodiments discussed in this disclosure may also be implemented in artificial-reality systems that include one or more NEDs. For example, as shown in FIG. 11, the AR system 1100 may include an eyewear device 1102 with a frame 1110 configured to hold a left display device 1115(B) and a right display device 1115(A) in front of a user's eyes. The display devices 1115(A) and 1115(B) may act together or independently to present an image or series of images to a user. While the AR system 1100 includes two displays, embodiments of this disclosure may be implemented in AR systems with a single NED or more than two NEDs.

In some embodiments, the AR system 1100 includes one or more sensors, such as the sensors 1140 and 1150 (examples of sensors 114, FIG. 1). The sensors 1140 and 1150 may generate measurement signals in response to motion of the AR system 1100 and may be located on substantially any portion of the frame 1110. Each sensor may be a position sensor, an inertial measurement unit (IMU), a depth camera assembly, or any combination thereof. The AR system 1100 may or may not include sensors or may include more than one sensor. In embodiments in which the sensors include an IMU, the IMU may generate calibration data based on measurement signals from the sensors. Examples of the sensors include, without limitation, accelerometers, gyroscopes, magnetometers, other suitable types of sensors that detect motion, sensors used for error correction of the IMU, or some combination thereof. Sensors are also discussed above with reference to FIG. 1.

The AR system 1100 may also include a microphone array with a plurality of acoustic sensors 1120(A)-1120(J), referred to collectively as the acoustic sensors 1120. The acoustic sensors 1120 may be transducers that detect air pressure variations induced by sound waves. Each acoustic sensor 1120 may be configured to detect sound and convert the detected sound into an electronic format (e.g., an analog or digital format). The microphone array in FIG. 11 may include, for example, ten acoustic sensors: 1120(A) and 1120(B), which may be designed to be placed inside a corresponding ear of the user, acoustic sensors 1120(C), 1120(D), 1120(E), 1120(F), 1120(G), and 1120(H), which may be positioned at various locations on the frame 1110, and/or acoustic sensors 1120(I) and 1120(J), which may be positioned on a corresponding neckband 1105. In some embodiments, the neckband 1105 is an example of a computer system.

The configuration of the acoustic sensors 1120 of the microphone array may vary. While the AR system 1100 is shown in FIG. 11 having ten acoustic sensors 1120, the number of acoustic sensors 1120 may be greater or less than ten. In some embodiments, using more acoustic sensors 1120 may increase the amount of audio information collected and/or the sensitivity and accuracy of the audio information. In contrast, using a lower number of acoustic sensors 1120 may decrease the computing power required by a controller 1125 to process the collected audio information. In addition, the position of each acoustic sensor 1120 of the microphone array may vary. For example, the position of an acoustic sensor 1120 may include a defined position on the user, a defined coordinate on the frame 1110, an orientation associated with each acoustic sensor, or some combination thereof.

The acoustic sensors 1120(A) and 1120(B) may be positioned on different parts of the user's ear, such as behind the pinna or within the auricle or fossa. In some embodiments, there are additional acoustic sensors on or surrounding the ear in addition to acoustic sensors 1120 inside the ear canal. Having an acoustic sensor positioned next to an ear canal of a user may enable the microphone array to collect information on how sounds arrive at the ear canal. By positioning at least two of the acoustic sensors 1120 on either side of a user's head (e.g., as binaural microphones), the AR device 1100 may simulate binaural hearing and capture a 3D stereo sound field around about a user's head. In some embodiments, the acoustic sensors 1120(A) and 1120(B) may be connected to the AR system 1100 via a wired connection, and in other embodiments, the acoustic sensors 1120(A) and 1120(B) may be connected to the AR system 1100 via a wireless connection (e.g., a Bluetooth connection). In still other embodiments, the acoustic sensors 1120(A) and 1120(B) may not be used at all in conjunction with the AR system 1100.

The acoustic sensors 1120 on the frame 1110 may be positioned along the length of the temples, across the bridge, above or below the display devices 1115(A) and 1115(B), or some combination thereof. The acoustic sensors 1120 may be oriented such that the microphone array is able to detect sounds in a wide range of directions surrounding the user wearing AR system 1100. In some embodiments, an optimization process may be performed during manufacturing of the AR system 1100 to determine relative positioning of each acoustic sensor 1120 in the microphone array.

The AR system 1100 may further include or be connected to an external device (e.g., a paired device), such as a neckband 1105. As shown, the neckband 1105 may be coupled to the eyewear device 1102 via one or more connectors 1130. The connectors 1130 may be wired or wireless connectors and may include electrical and/or non-electrical (e.g., structural) components. In some cases, the eyewear device 1102 and the neckband 1105 operate independently without any wired or wireless connection between them. While FIG. 11 illustrates the components of the eyewear device 1102 and the neckband 1105 in example locations on the eyewear device 1102 and the neckband 1105, the components may be located elsewhere and/or distributed differently on the eyewear device 1102 and/or on the neckband 1105. In some embodiments, the components of the eyewear device 1102 and the neckband 1105 may be located on one or more additional peripheral devices paired with the eyewear device 1102, the neckband 1105, or some combination thereof. Furthermore, the neckband 1105 generally represents any type or form of paired device. Thus, the following discussion of neckband 1105 may also apply to various other paired devices, such as smart watches, smart phones, wrist bands, other wearable devices, hand-held controllers, tablet computers, or laptop computers.

Pairing external devices, such as a neckband 1105, with AR eyewear devices may enable the eyewear devices to achieve the form factor of a pair of glasses while still providing sufficient battery and computation power for expanded capabilities. Some or all of the battery power, computational resources, and/or additional features of the AR system 1100 may be provided by a paired device or shared between a paired device and an eyewear device, thus reducing the weight, heat profile, and form factor of the eyewear device overall while still retaining desired functionality. For example, the neckband 1105 may allow components that would otherwise be included on an eyewear device to be included in the neckband 1105 because users may tolerate a heavier weight load on their shoulders than they would tolerate on their heads. The neckband 1105 may also have a larger surface area over which to diffuse and disperse heat to the ambient environment. Thus, the neckband 1105 may allow for greater battery and computation capacity than might otherwise have been possible on a stand-alone eyewear device. Because weight carried in the neckband 1105 may be less invasive to a user than weight carried in the eyewear device 1102, a user may tolerate wearing a lighter eyewear device and carrying or wearing the paired device for greater lengths of time than the user would tolerate wearing a heavy standalone eyewear device, thereby enabling an artificial-reality environment to be incorporated more fully into a user's day-to-day activities.

The neckband 1105 may be communicatively coupled with the eyewear device 1102 and/or to other devices (e.g., a wearable device). The other devices may provide certain functions (e.g., tracking, localizing, depth mapping, processing, storage, etc.) to the AR system 1100. In the embodiment of FIG. 11, the neckband 1105 includes two acoustic sensors 1120(I) and 1120(J), which are part of the microphone array (or potentially form their own microphone subarray). The neckband 1105 includes a controller 1125 and a power source 1135.

The acoustic sensors 1120(I) and 1120(J) of the neckband 1105 may be configured to detect sound and convert the detected sound into an electronic format (analog or digital). In the embodiment of FIG. 11, the acoustic sensors 1120(I) and 1120(J) are positioned on the neckband 1105, thereby increasing the distance between neckband acoustic sensors 1120(I) and 1120(J) and the other acoustic sensors 1120 positioned on the eyewear device 1102. In some cases, increasing the distance between the acoustic sensors 1120 of the microphone array improves the accuracy of beamforming performed via the microphone array. For example, if a sound is detected by the acoustic sensors 1120(C) and 1120(D) and the distance between acoustic sensors 1120(C) and 1120(D) is greater than, for example, the distance between the acoustic sensors 1120(D) and 1120(E), the determined source location of the detected sound may be more accurate than if the sound had been detected by the acoustic sensors 1120(D) and 1120(E).

The controller 1125 of the neckband 1105 may process information generated by the sensors on the neckband 1105 and/or the AR system 1100. For example, the controller 1125 may process information from the microphone array, which describes sounds detected by the microphone array. For each detected sound, the controller 1125 may perform a direction of arrival (DOA) estimation to estimate a direction from which the detected sound arrived at the microphone array. As the microphone array detects sounds, the controller 1125 may populate an audio data set with the information. In embodiments in which the AR system 1100 includes an IMU, the controller 1125 may compute all inertial and spatial calculations from the IMU located on the eyewear device 1102. The connector 1130 may convey information between the AR system 1100 and the neckband 1105 and between the AR system 1100 and the controller 1125. The information may be in the form of optical data, electrical data, wireless data, or any other transmittable data form. Moving the processing of information generated by the AR system 1100 to the neckband 1105 may reduce weight and heat in the eyewear device 1102, making it more comfortable to a user.

The power source 1135 in the neckband 1105 may provide power to the eyewear device 1102 and/or to the neckband 1105. The power source 1135 may include, without limitation, lithium-ion batteries, lithium-polymer batteries, primary lithium batteries, alkaline batteries, or any other form of power storage. In some cases, the power source 1135 may be a wired power source. Including the power source 1135 on the neckband 1105 instead of on the eyewear device 1102 may help better distribute the weight and heat generated by the power source 1135.

As noted, some artificial-reality systems may, instead of blending an artificial-reality with actual reality, substantially replace one or more of a user's sensory perceptions of the real world with a virtual experience. One example of this type of system is a head-worn display system, such as the VR system 1200 in FIG. 12, which mostly or completely covers a user's field of view. The VR system 1200 may include a front rigid body 1202 and a band 1004 shaped to fit around a user's head. In some embodiments, the VR system 1200 includes output audio transducers 1206(A) and 1206(B), as shown in FIG. 12. Furthermore, while not shown in FIG. 12, the front rigid body 1202 may include one or more electronic elements, including one or more electronic displays, one or more IMUs, one or more tracking emitters or detectors, and/or any other suitable device or system for creating an artificial-reality experience.

Artificial-reality systems may include a variety of types of visual feedback mechanisms. For example, display devices in the AR system 1100 and/or the VR system 1200 may include one or more liquid-crystal displays (LCDs), light emitting diode (LED) displays, organic LED (OLED) displays, and/or any other suitable type of display screen. Artificial-reality systems may include a single display screen for both eyes or may provide a display screen for each eye, which may allow for additional flexibility for varifocal adjustments or for correcting a user's refractive error. Some artificial-reality systems also include optical subsystems having one or more lenses (e.g., conventional concave or convex lenses, Fresnel lenses, or adjustable liquid lenses) through which a user may view a display screen. These systems and mechanisms are discussed in further detail above with reference to FIG. 1.

In addition to or instead of using display screens, some artificial-reality systems include one or more projection systems. For example, display devices in the AR system 1100 and/or the VR system 1200 may include micro-LED projectors that project light (e.g., using a waveguide) into display devices, such as clear combiner lenses that allow ambient light to pass through. The display devices may refract the projected light toward a user's pupil and may enable a user to simultaneously view both artificial-reality content and the real world. Artificial-reality systems may also be configured with any other suitable type or form of image projection system.

Artificial-reality systems may also include various types of computer vision components and subsystems. For example, the AR system 1000, the AR system 1100, and/or the VR system 1200 may include one or more optical sensors such as two-dimensional (2D) or three-dimensional (3D) cameras, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

Artificial-reality systems may also include one or more input and/or output audio transducers. In the examples shown in FIGS. 10 and 12, the output audio transducers 1008(A), 1008(B), 1206(A), and 1206(B) may include voice coil speakers, ribbon speakers, electrostatic speakers, piezoelectric speakers, bone conduction transducers, cartilage conduction transducers, and/or any other suitable type or form of audio transducer. Similarly, the input audio transducers 1010 may include condenser microphones, dynamic microphones, ribbon microphones, and/or any other type or form of input transducer. In some embodiments, a single transducer may be used for both audio input and audio output.

The artificial reality systems shown in FIGS. 10-12 may include tactile (i.e., haptic) feedback systems, which may be incorporated into headwear, gloves, body suits, handheld controllers, environmental devices (e.g., chairs or floor-mats), and/or any other type of device or system, such as the wearable devices 120 discussed herein. Additionally, in some embodiments, the haptic feedback systems may be incorporated with the artificial reality systems (e.g., systems 1000, 1100, and 1200 may include the wearable device 120 shown in FIG. 1). Haptic feedback systems may provide various types of cutaneous feedback, including vibration, force, traction, shear, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independently of other artificial-reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, or business enterprises), entertainment purposes (e.g., for playing video games, listening to music, or watching video content), and/or for accessibility purposes (e.g., as hearing aids or vision aids). The embodiments disclosed herein may enable or enhance a user's artificial-reality experience in one or more of these contexts and environments and/or in other contexts and environments.

Some AR systems map a user's environment using techniques referred to as "simultaneous location and mapping" (SLAM). SLAM mapping and location identifying techniques may involve a variety of hardware and software tools that can create or update a map of an environment while simultaneously keeping track of a device's or a user's location and/or orientation within the mapped environment. SLAM may use many different types of sensors to create a map and determine a device's or a user's position within the map.

SLAM techniques may, for example, implement optical sensors to determine a device's or a user's location, position, or orientation. Radios, including Wi-Fi, Bluetooth, global positioning system (GPS), cellular or other communication devices may also be used to determine a user's location relative to a radio transceiver or group of transceivers (e.g., a Wi-Fi router or group of GPS satellites). Acoustic sensors such as microphone arrays or 2D or 3D sonar sensors may also be used to determine a user's location within an environment. AR and VR devices (such as the systems 1000, 1100, and 1200) may incorporate any or all of these types of sensors to perform SLAM operations such as creating and continually updating maps of a device's or a user's current environment. In at least some of the embodiments described herein, SLAM data generated by these sensors may be referred to as "environmental data" and may indicate a device's or a user's current environment. This data may be stored in a local or remote data store (e.g., a cloud data store) and may be provided to a user's artificial-reality device on demand.

When a user is wearing an AR headset or VR headset in a given environment, the user may be interacting with other users or other electronic devices that serve as audio sources. In some cases, it may be desirable to determine where the audio sources are located relative to the user and then present the audio sources to the user as if they were coming from the location of the audio source. The process of determining where the audio sources are located relative to the user may be referred to herein as "localization," and the process of rendering playback of the audio source signal to appear as if it is coming from a specific direction may be referred to herein as "spatialization."

Localizing an audio source may be performed in a variety of different ways. In some cases, an AR or VR headset may initiate a Direction of Arrival ("DOA") analysis to determine the location of a sound source. The DOA analysis may include analyzing the intensity, spectra, and/or arrival time of each sound at the AR/VR device to determine the direction from which the sound originated. In some cases, the DOA analysis may include any suitable algorithm for analyzing the surrounding acoustic environment in which the artificial-reality device is located.

For example, the DOA analysis may be designed to receive input signals from a microphone and apply digital signal processing algorithms to the input signals to estimate the direction of arrival. These algorithms may include, for example, delay and sum algorithms where the input signal is sampled, and the resulting weighted and delayed versions of the sampled signal are averaged together to determine a direction of arrival. A least mean squared (LMS) algorithm may also be implemented to create an adaptive filter. This adaptive filter may then be used to identify differences in signal intensity, for example, or differences in time of arrival. These differences may then be used to estimate the direction of arrival. In another embodiment, the DOA may be determined by converting the input signals into the frequency domain and selecting specific bins within the time-frequency (TF) domain to process. Each selected TF bin may be processed to determine whether that bin includes a portion of the audio spectrum with a direct-path audio signal. Those bins having a portion of the direct-path signal may then be analyzed to identify the angle at which a microphone array received the direct-path audio signal. The determined angle may then be used to identify the direction of arrival for the received input signal. Other algorithms not listed above may also be used alone or in combination with the above algorithms to determine DOA.

In some embodiments, different users may perceive the source of a sound as coming from slightly different locations. This may be the result of each user having a unique head-related transfer function (HRTF), which may be dictated by a user's anatomy, including ear canal length and the positioning of the ear drum. The artificial-reality device may provide an alignment and orientation guide, which the user may follow to customize the sound signal presented to the user based on a personal HRTF. In some embodiments, an AR or VR device may implement one or more microphones to listen to sounds within the user's environment. The AR or VR device may use a variety of different array transfer functions (ATFs) (e.g., any of the DOA algorithms identified above) to estimate the direction of arrival for the sounds. Once the direction of arrival has been determined, the artificial-reality device may play back sounds to the user according to the user's unique HRTF. Accordingly, the DOA estimation generated using an ATF may be used to determine the direction from which the sounds are to be played from. The playback sounds may be further refined based on how that specific user hears sounds according to the HRTF.

In addition to or as an alternative to performing a DOA estimation, an artificial-reality device may perform localization based on information received from other types of sensors. These sensors may include cameras, infrared radiation (IR) sensors, heat sensors, motion sensors, global positioning system (GPS) receivers, or in some cases, sensor that detect a user's eye movements. For example, an artificial-reality device may include an eye tracker or gaze detector that determines where a user is looking. Often, a user's eyes will look at the source of a sound, if only briefly. Such clues provided by the user's eyes may further aid in determining the location of a sound source. Other sensors such as cameras, heat sensors, and IR sensors may also indicate the location of a user, the location of an electronic device, or the location of another sound source. Any or all of the above methods may be used individually or in combination to determine the location of a sound source and may further be used to update the location of a sound source over time.

Some embodiments may implement the determined DOA to generate a more customized output audio signal for the user. For instance, an acoustic transfer function may characterize or define how a sound is received from a given location. More specifically, an acoustic transfer function may define the relationship between parameters of a sound at its source location and the parameters by which the sound signal is detected (e.g., detected by a microphone array or detected by a user's ear). An artificial-reality device may include one or more acoustic sensors that detect sounds within range of the device. A controller of the artificial-reality device may estimate a DOA for the detected sounds (e.g., using any of the methods identified above) and, based on the parameters of the detected sounds, may generate an acoustic transfer function that is specific to the location of the device. This customized acoustic transfer function may thus be used to generate a spatialized output audio signal where the sound is perceived as coming from a specific location.

Once the location of the sound source or sources is known, the artificial-reality device may re-render (i.e., spatialize) the sound signals to sound as if coming from the direction of that sound source. The artificial-reality device may apply filters or other digital signal processing that alter the intensity, spectra, or arrival time of the sound signal. The digital signal processing may be applied in such a way that the sound signal is perceived as originating from the determined location. The artificial-reality device may amplify or subdue certain frequencies or change the time that the signal arrives at each ear. In some cases, the artificial-reality device may create an acoustic transfer function that is specific to the location of the device and the detected direction of arrival of the sound signal. In some embodiments, the artificial-reality device may re-render the source signal in a stereo device or multi-speaker device (e.g., a surround sound device). In such cases, separate and distinct audio signals may be sent to each speaker. Each of these audio signals may be altered according to a user's HRTF and according to measurements of the user's location and the location of the sound source to sound as if they are coming from the determined location of the sound source. Accordingly, in this manner, the artificial-reality device (or speakers associated with the device) may re-render an audio signal to sound as if originating from a specific location.

Some embodiments include: a haptic device comprising: a wearable structure to be worn on a portion of a user's body; and an inflatable bladder, coupled to the wearable structure at a target location, that includes opposing first and second surfaces, the inflatable bladder being configured to receive a fluid from a source, wherein the first surface of the inflatable bladder includes a plurality of barbs positioned to interact with the user's body at the target location, the plurality of barbs being configured to protrude from the first surface in response to the inflatable bladder receiving the fluid from the source.

In some embodiments, of the haptic device, the first surface of the inflatable bladder transitions from a concave shape to a convex shape in response to the inflatable bladder receiving the fluid from the source.

In some embodiments, of the haptic device, the convex shape of the first surface causes the plurality of barbs to protrude from the first surface.

In some embodiments, of the haptic device, the concave shape of the first surface of the inflatable bladder complements a profile of the user's body at the target location.

In some embodiments, of the haptic device: barbs in the plurality of barbs are arranged in a predefined pattern; and the predefined pattern is defined according to a profile of the user's body at the target location.

In some embodiments, of the haptic device, respective shapes of the barbs in the plurality of barbs are also defined according to the profile of the user's body at the target location.

In some embodiments, of the haptic device, respective depths of the barbs in the plurality of barbs are also defined according to the profile of the user's body at the target location.

In some embodiments, of the haptic device: the first surface of the inflatable bladder is made from an elastic material; and the second surface of the inflatable bladder is (i) made from an inelastic material and (ii) positioned to not interact with the portion of the user's body.

In some embodiments, of the haptic device, a roughness of the first surface of the inflatable bladder increases with a fluid pressure inside the inflatable bladder.

In some embodiments, of the haptic device, the first surface of the inflatable bladder is configured to have a maximum roughness when the fluid pressure inside the inflatable bladder reaches a maximum pressure.

In some embodiments, of the haptic device, the plurality of barbs included with the first surface of the inflatable bladder is further configured to impart a haptic stimulation to the user's body at the target location in response to the inflatable bladder receiving the fluid from the source.

In some embodiments, of the haptic device: the first surface of the inflatable bladder has a first texture when a fluid pressure inside the inflatable bladder is at a first pressure; and the first surface of the inflatable bladder has a second texture when the fluid pressure inside the inflatable bladder is at a second pressure greater than the first pressure.

In some embodiments, of the haptic device: when the inflatable bladder is in a first pressurized state, the first surface of the inflatable bladder is adjacent to the second surface of the inflatable bladder; and when the inflatable bladder is in a second pressurized state, the first surface of the inflatable bladder bulges away from the second surface of the inflatable bladder, causing the plurality of barbs to protrude from the first surface.

In some embodiments, of the haptic device: when the inflatable bladder is in the first pressurized state, first distances separate barbs in the plurality of barbs; and when the inflatable bladder is in the second pressurized state, second distances greater than the first distances separate the barbs in the plurality of barbs.

In some embodiments, of the haptic device, the inflatable bladder is a first inflatable bladder and the plurality of barbs is a first plurality of barbs, and the haptic device further comprises: a second inflatable bladder, coupled to the wearable structure at a different target location, configured to receive the fluid from the source, wherein: a surface of the second inflatable bladder includes a second plurality of barbs positioned to interact with the user's body at the different target location, the second plurality of barbs being configured to protrude from the surface in response to the second inflatable bladder receiving the fluid from the source, and the first plurality of barbs are arranged in a pattern that differs from a pattern of the second plurality of barbs.

Some embodiments include an artificial-reality device comprising: a pressure source; a computer in communication with the pressure source; and a haptic device that includes: a wearable structure to be worn on a portion of a user's body; and an inflatable bladder, coupled to the wearable structure at a target location, that includes opposing first and second surfaces, the inflatable bladder being configured to receive a fluid from the pressure source, wherein the first surface of the inflatable bladder includes a plurality of barbs positioned to interact with the user's body at the target location, the plurality of barbs being configured to protrude from the first surface in response to the inflatable bladder receiving the fluid from the pressure source.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software, or any combination thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. A haptic device comprising:
 a wearable structure to be worn on a portion of a user's body; and
 at least one inflatable bladder, coupled to the wearable structure, that includes two or more pockets positioned at a target location on the wearable structure,
 wherein:
  the two or more pockets are configured to, when inflated, impart one or more directional forces onto the user at the target location that impede movement of the portion of the user's body;
  the one or more directional forces are caused by the two or more pockets interfering with each other, when inflated; and
  a magnitude of the one or more directional forces corresponds to a fluid pressure inside the two or more pockets and a change in geometry of the two or more pockets caused by the two or more pockets interfering with each other.

2. The haptic device of claim 1, wherein two or more pockets comprise:
 a first pocket with an end portion and a body portion; and
 a second pocket with an end portion and a body portion, wherein: (i) the end portion of the second pocket is coupled with the end portion of the first pocket to form a connection point, and (ii) the body portion of the second pocket is decoupled from the body portion of the first pocket.

3. The haptic device of claim 2, wherein:
when the two or more pockets are inflated, the first and second pockets are configured to expand such that the body portion of the second pocket and the body portion of the first pocket fan out away from the connection point; and
when the two or more pockets are not inflated, the first and second pockets are configured to collapse such that the body portion of the second pocket and the body portion of the first pocket are adjacent to each other.

4. The haptic device of claim 1, wherein:
the at least one inflatable bladder further comprises an elongated substrate forming a first side of the respective inflatable bladder; and
the two or more pockets (i) are coupled to and distributed along a length of the elongated substrate and (ii) form a second side of the respective inflatable bladder.

5. The haptic device of claim 4, wherein:
when the two or more pockets are inflated, each pocket is configured to expand and interfere with at least one other pocket of the two or more pockets; and
when the two or more pockets are not inflated, the two or more pockets do not impede free movement of the portion of the user's body.

6. The haptic device of claim 4, wherein:
the elongated substrate has a first elasticity; and
the two or more pockets have a second elasticity that is greater than the first elasticity.

7. The haptic device of claim 6, wherein:
the elongated substrate is made from an inelastic textile; and
the two or more pockets are made from an elastic polymer.

8. The haptic device of claim 4, wherein:
the portion of the user's body is a hand of the user; and
the elongated substrate is sized to fit along a palmar side of a first finger of the user's hand.

9. The haptic device of claim 1, wherein:
the portion of the user's body is a hand of the user;
the target location is a finger joint on the user's hand; and
the one or more directional forces imparted onto the user at the target location impede flexion of the user's finger.

10. The haptic device of claim 1, further comprising a grounding assembly that is configured to secure the wearable structure and the at least one inflatable bladder to the user's body.

11. The haptic device of claim 1, wherein:
the two or more pockets have a predefined shape when inflated to a predefined pressure; and
the predefined shape is dependent, at least in part, on a wall thickness of each pocket of the two or more pockets.

12. The haptic device of claim 1, wherein:
the at least one inflatable bladder is fluidically coupled to a source; and
the two or more pockets are further configured to (i) receive a fluid from the source and (ii) expand in proportion with a fluid pressure inside each pocket.

13. The haptic device of claim 12, further comprises a switchable valve that is configured to switch between an open state and a closed state,
wherein the switchable valve prevents the fluid from exiting the two or more pockets when in the closed state.

14. The haptic device of claim 12, wherein:
the source is in communication with a computing device; and
the source is configured to change the fluid pressure of the two or more pockets in response to receiving one or more signals from the computing device.

15. The haptic device of claim 14, wherein:
the computing device is in communication with a head-mounted display that presents content to the user, the head-mounted display including an electronic display; and
the one or more signals correspond to content displayed on the electronic display.

16. The haptic device of claim 14, further comprising one or more sensors, coupled to the wearable structure, configured to generate spatial and motion data corresponding to the user's movements,
wherein the spatial and motion data are communicated to the computing device.

17. The haptic device of claim 16, wherein:
the one or more signals further correspond to the spatial and motion data corresponding to the user's movements; and
the one or more signals are generated by the computing device to impede movement of the portion of the user's body.

18. The haptic device of claim 1, wherein the one or more directional forces imparted onto the user at the target location simulate forces induced by physical objects at the target location during natural-object interaction.

19. An artificial-reality device comprising: a pressure source;
a computer in communication with the pressure source; and
a haptic device that includes:
a wearable structure configured to be worn on a portion of a user's body; and
at least one inflatable bladder, coupled to the wearable structure, that includes two or more pockets positioned at a target location on the wearable structure, wherein the two or more pockets are configured to, when inflated by the pressure source, impart one or more directional forces onto the user at the target location that impede movement of the portion of the user's body, and wherein a magnitude of the one or more directional forces corresponds to a fluid pressure inside the two or more pockets and a change in geometry of the two or more pockets caused by the two or more pockets interfering with each other.

* * * * *